United States Patent [19]

Pirkle et al.

[11] Patent Number: 5,256,293
[45] Date of Patent: Oct. 26, 1993

[54] SEPARATION OF ENANTIOMERS OF NON-STEROIDAL ANTI-INFLAMMATORY DRUGS AND CHIRAL SELECTOR THEREFOR

[75] Inventors: William H. Pirkle, Champaign; Christopher J. Welch, Northbrook, both of Ill.; Bo R. Lamm, Goteborg, Sweden

[73] Assignee: Research Corporation Technologies, Inc., Tucson, Ariz.

[21] Appl. No.: 847,449

[22] Filed: Mar. 9, 1992

Related U.S. Application Data

[63] Continuation-in-part of Ser. No. 763,043, Sep. 20, 1991, abandoned.

[51] Int. Cl.⁵ .............................................. B01D 15/08
[52] U.S. Cl. ................................... 210/635; 210/656; 210/198.2; 210/502.1; 502/401; 502/439
[58] Field of Search ..................... 210/635, 656, 198.2, 210/502.1; 435/280; 502/401, 402, 404, 439

[56] References Cited

U.S. PATENT DOCUMENTS

| | | | |
|---|---|---|---|
| 4,318,819 | 3/1982 | Malloy | 210/635 |
| 4,318,820 | 3/1982 | Malloy | 210/635 |
| 4,322,310 | 3/1982 | House | 210/635 |
| 4,512,898 | 4/1985 | Oi | 210/656 |
| 4,604,207 | 8/1986 | Oi | 210/635 |
| 4,818,394 | 4/1989 | Okamoto | 210/656 |
| 4,824,950 | 4/1989 | Barcza | 546/14 |
| 4,909,935 | 3/1990 | Bradshaw et al. | 210/198.2 |
| 4,919,803 | 4/1990 | Doyle et al. | 210/198.2 |
| 5,080,795 | 1/1992 | Pirkle | 210/643 |

FOREIGN PATENT DOCUMENTS

0299793  1/1989  European Pat. Off. ......... 210/198.2

OTHER PUBLICATIONS

Wainer, et al., "Resolution of Norephedrine as its 2-oxazolidone Derivative: Enantiomeric Separation on a Chiral High-Performance Liquid Chromatographic Stationary Phase and Preparative Regeneration of the Resolved Isomers", 268, J. of Chromatogr., 107–111 (1983).

Wainer, et al., "Application of High-Performance Liquid Chromatographic Chiral Stationary Phases to Pharmaceutical Analysis: Structural and Conformational Effects in the Direct Enantiomeric Resolution of α-Methylarylacetic Acid Anti-Inflammatory Agents", 284, J. of Chromatogr., 117–124 (1984).

Yang, et al., "Application of High-Performance Liquid Chromatographic Chiral Stationary Phases to Pharmaceutical Analysis: Resolution of Enantiomeric Barbiturates, Succinimides and Related Molecules on Four Commercially Available Chiral Stationary Phases", 324, J. of Chromatogr., 444–449 (1985).

"One Optical Isomer Without the Other", Chemical Week, 28–29, Feb. 13, 1985.

Doyle, "Analytical Criteria for Chiral HPLC: Where We Are Now", Anyl. Item 44 (Undated).

Doyle, et al., "The Resolution of Enantiomeric Drugs Using HPLC Chiral Stationary Phases", Pharmaceutical Technology, 28–32, (Feb. 1985).

Wainer, et al., "The Application of HPLC Chiral Stationary Phases to Pharmaceutical Analysis: The Resolution of Some Tropic Acid Derivatives", 7(4), J. of Liquid Chromatogr., 731–741 (1984).

Perry, et al., "Chiral Separations by HPLC. Theory and Practice: Developments with the Pirkle Covalent JPLC Column", No. 939 (Undated).

(List continued on next page.)

Primary Examiner—Ernest G. Therkorn
Attorney, Agent, or Firm—Scully, Scott, Murphy & Presser

[57] ABSTRACT

The invention relates to a chiral selector useful in separating underivatized enantiomers of nonsterodial anti-inflammatory agents, particularly naproxen and other arylacetic acid compounds, and relates to a process for achieving such separation utilizing the chiral selector, which is also useful in achieving the enantiomeric separation of amines, alcohol derivatives, epoxides and sulfoxides. The invention is also directed to an apparatus which comprises the chiral selectors.

4 Claims, No Drawings

OTHER PUBLICATIONS

Wainer, et al., "Stereoisomeric Separations: Use of Chiral Stationary Phases to Resolve Molecules of Pharmacological Interest", 2, No. 2, LC, 88–89 (Undated).

Hermansson, et al., "Direct Liquid Chromatographic Resolution of Acidic Drugs Using a Chiral α1-Acid Glycoprotein Column (Enantiopac®)", 9(2 & 3), J. of Liquid Chromatogr., 621–639 (1986).

Pettersson, et al., "Improved Resolution of Enantiomers of Naproxen by the Simultaneous Use of a Chiral Stationary Phase and a Chiral Additive in the Mobile Phase", 435, J. of Chromatogr., 225–228 (1988).

Bojarski, "Chromatography of Enantiomers of 2-Arylpropionic Acids", 12(14), 2685–2706 (1989).

Pirkle, et al., "The Separation of the Enantiomers of a Variety of Non-Steroidal Anti-Inflammatory Drugs (NSAIDS) as Their Anilide Derivatives Using a Chiral Stationary Phase", 13(11), J. of Liquid Chromatogr., 2123–2134 (1990).

Pirkle, et al., "Improved Chiral Stationary Phase for the Separation of the Enantiomers of Chiral Acids as Their Anilide Derivatives", 471, J. of Chromatogr., 271–281 (1989).

Pirkle, et al., "A Chiral Stationary Phase Which Affords Unusually High Levels of Enantioselectivity", 3, Chirality, 183–187 (1991).

Pirkle, et al., "Use of Achiral Ion-Pairing Reagents with Chiral Stationary Phases", 479, J. of Chromatogr., 377–386 (1989).

Pirkle, et al., "An Improved Chiral Stationary Phase for the Facile Separation of Enantiomers", 441, J. of Chromatogr., 311–322 (1988).

Rubin, et al., "Chiral Recognition in Aqueous Solution. Search for Water-Soluble Chiral Hosts with Apolar Binding Sites", 51, J. Org. Chem., 3270–3278 (1986).

Castro, et al., "Chiral Recognition in Clefts and Cyclophane Cavities Shaped by the 1,1'-Binaphthyl Major Groove", 54, J. Org. Chem., 5835–5838, (1989).

Georgiadis, et al., "Synthesis and Complexation Properties of a Water-Soluble Optically Active Cyclophane Incorporating a 4-Naphthyl-1,2,3,4-tetrahydroisoquinoline Unit as a Chiral Spacer", 56, J. Org. Chem., 3362–3369 (1991).

Dharanipragada, et al., "A Novel Optically Active Host: Design, Computer Graphics, Synthesis, and Diastereomeric Complex Formation in Aqueous Solution", 110, J. Am. Chem. Soc., 1679–1690 (1988).

Oi, et al., "Direct Separation of Underivatized α-methylarylacetic Acid Enantiomers by High Performance Liquid Chromatography with Chiral Stationary Phase", 35, Bunseki Kagaku, 312–313 (1986) (Japan).

Pirkle, et al., "A Convenient Void Volume Marker for Several Chiral HPLC Columns", 14(1), J. of Liquid Chromatogr., 1–8 (1991).

Dharanipragada, et al., "Diasteroemeric Complex Formation Between a Novel Optically Active Host and Naproxen in Aqueous Solution", 28(22), Tetrahedron Letters, 2443–2446 (1987).

Schroeter, et al., "Uber Die Hydrierung Des Phenanthrens", 62, Ber. Der. Deutschen Chem., 645–658 (1929) (Germany).

Pirkle, et al., "Systematic Studies of Chiral Recognition Mechanisms", Chiral Separations, 23–35 (1988) Edited by Stevenson of Plenum Press, New York.

Crossland, et al., "A Facile Synthesis of Methanesulfonate Esters", 35, J. Org. Chem., 3195–3196 (1970).

William H. Pirkle, et al., "Design, Synthesis and Evaluation of an Improved Enantioselective Naproxen Selector", *J. Org. Chem.* 57, No. 14, pp. 3854–3860 (Jul. 3, 1992).

William H. Pirkle, et al. (1992) "An Improved Chiral Stationary Phase for the Chromatographic Separation of Underivatized Naproxen Enantiomers", *Journal of Liquid Chromatography* 15, No. 11, pp. 1947–1955.

SEPARATION OF ENANTIOMERS OF NON-STEROIDAL ANTI-INFLAMMATORY DRUGS AND CHIRAL SELECTOR THEREFOR

This invention was made with Government support under Grant CHE-8714950 awarded by the National Science Foundation. The Government has certain rights in the invention.

This application is a continuation-in-part of U.S. patent application Ser. No. 763,043 filed Sep. 20, 1991, now abandoned.

BACKGROUND OF THE INVENTION

1. Field of the Invention

The present invention relates to the separation of enantiomers, i.e., those isomers in which the arrangement of atoms or groups is such that the two molecules are not super-imposable. The invention more particularly relates to a chiral selector useful, for example, as a chiral stationary phase (CSP) in the liquid chromatographic separation (HPLC) of enantiomers of non-steroidal anti-inflammatory agents.

2. Description of the Prior Art

Stereoisomers are those molecules which differ from each other only in the way their atoms are oriented in space. Stereoisomers are generally classified as diastereomers or enantiomers; the latter embracing those which are mirror-images of each other, the former being those which are not. The particular arrangement of atoms that characterize a particular stereoisomer is known as its optical configuration, specified by known sequencing rules as, for example, either + or − (also D or L) and/or R or S.

Though differing only in orientation, the practical effects of stereoisomerism are important. For example, the biological and pharmaceutical activities of many compounds are strongly influenced by the particular configuration involved. Indeed, many compounds are only of widespread utility when employed in a given stereoisomeric form.

Living organisms usually produce only one enantiomer of a pair. Thus only (−)-2-methyl-1-butanol is formed in yeast fermentation of starches; only (+)-lactic acid is formed in the contraction of muscle; fruit juices contain only (−)-malic acid, and only (−)-quinine is obtained from the cinchona tree. In biological systems, stereochemical specificity is the rule rather than the exception, since the catalytic enzymes, which are so important in such systems, are optically active For example, the sugar (+)-glucose plays an important role in animal metabolism and is the basic raw material in the fermentation industry; however, its optical counterpart, or antipode, (−)-glucose, is neither metabolized by animals nor fermented by yeasts. Other examples in this regard include the mold *Penicillium glaucum*, which will only consume the (+)-enantiomer of an enantiomeric mixture of tartaric acid, leaving the (−)-enantiomer intact. Also, only one stereoisomer of chloromycetin is an antibiotic; and (+)-ephedrine not only does not have any drug activity, but it interferes with the drug activity of its antipode. Finally, in the world of essences, the enantiomer (−)-carvone provides oil of spearmint with its distinctive odor, while its optical counterpart (+)-carvone provides the essence of caraway.

Accordingly, it is desirable and oftentimes essential to separate stereoisomers in order to obtain the useful version of a compound that is optically active.

Separation in this regard is generally not a problem when diastereomers are involved: diastereomers have different physical properties, such as melting points, boiling points, solubilities in a given solvent, densities, refractive indices etc. Hence, diastereomers are normally separated from one another by conventional methods, such as fractional distillation, fractional crystallization, chromatography.

Enantiomers, on the other hand, present a special problem because their physical properties are identical. Thus they cannot as a rule—and especially so when in the form of a racemic mixture—be separated by ordinary methods: not by fractional distillation, because their boiling points are identical; not by conventional crystallization because (unless the solvent is optically active) their solubilities are identical; not by conventional chromatography because (unless the adsorbent is optically active) they are held equally onto the adsorbent. The problem of separating enantiomers is further exacerbated by the fact that conventional synthetic techniques almost always produce a mixture of enantiomers. When a mixture comprises equal amounts of enantiomers having opposite optical configurations, it is called a racemate; separation of a racemate into its respective enantiomers is generally known as a resolution, and is a process of considerable importance.

Various techniques for separating enantiomers are known. Most, however, are directed to small, analytical quantities, meaning that other drawbacks aside, when applied to preparative scale amounts (the milligram to kilogram range) a loss of resolution occurs. Hand separation, the oldest method of resolution, is not only impractical but can almost never be used since racemates seldom form mixtures of crystals recognizable as mirror images.

Another method, known as indirect separation, involves the conversion of a mixture of enantiomers—the racemate—into a mixture of diastereomers. The conversion is accomplished by reacting the enantiomers with an optically pure derivatizing agent. The resultant diastereomers are then separated from one another by taking advantage of their different physical properties. Once separated by, for example, fractional crystallization, or more commonly chromatography, the diastereomers are re-converted back into the corresponding enantiomers, which are now optically pure. Though achieving the requisite separation, the indirect method suffers in that it is time consuming and can require large quantities of optically pure derivatizing agent which can be expensive and is oftentimes not recoverable. Moreover, the de-derivatizing step may itself result in racemization thus defeating the purpose of the separation earlier achieved.

A more current method that avoids some of the drawbacks attendant the indirect method is known as the direct method of separation. The direct method, much like the indirect method, involves the formation of a diastereomeric species. However, unlike the indirect method, this species is transient, with the stability of one species differing from the other.

In one application of the direct method, the mixture of enantiomers is allowed to interact with a chiral stationary phase which, for example, could reside in a chromatographic column. The enantiomer that interacts more strongly with the chiral stationary phase will have a longer residence time, hence a separation of enantiomers will occur. When the mode of interaction with the chiral stationary phase can be characterized, the elution order can be predicted. Examples of chiral stationary phases include those based upon (L)-N-(3,5-dinitrobenzoyl)leucine, which is useful in separating enantiomers of N-aryl derivatized amino acids and esters, and those based upon (L)-N-(1-naphthyl)leucine which has been used to effectively separate N-(3,5-dinitrobenzoyl) derivatized amino compounds. HPLC columns packed with silica-bonded CSP's of a variety of pi-electron acceptors and pi-electron donors—including derivatives of phenylglycine, leucine, naphthylalanine and naphthylleucine are commercially available from Regis Chemical Company, Morton Grove, Ill.

In another application of the direct method, disclosed in copending and commonly assigned patent application Ser. No. 528,007, filed May 23, 1990, now U.S. Pat. No. 5,080,795, enantiomers of such compounds as amino acids, amino esters, alcohols, amines, sulfonic acids or derivatives thereof are separated by means of a liquid membrane containing a chiral carrier, such as the derivatized amino acid (S)-N-(1-naphthyl)leucine octadecyl ester. The chiral carrier is capable of forming a stable complex with one of the enantiomers. The liquid membrane is located on one side of a semi-permeable barrier, and the mixture of enantiomers is located on the other side of the barrier. The liquid membrane containing the chiral carrier impregnates the semi-permeable barrier under conditions effective to permit or cause a stable complex between the chiral carrier and one of the enantiomers to form in the barrier. The liquid membrane containing the stable complex is passed to a second location where the conditions are effective to dissociate the stable complex, allowing the recovery of the complex-forming enantiomer to take place In one embodiment of this application, a hollow fiber membrane is employed as the semi-permeable barrier.

It is widely recognized that stereoisomers of pharmaceutical agents may have drastically different pharmacological potencies or actions. Among those pharmaceutical agents known to elicit differing physiological responses depending on the optical configuration used are the anti-phlogistics, which are those drugs used to counteract inflammation. Antiphlogistics are generally divided into two classes: nonsteroidal anti-inflammatory agents (NSAIAs), which are generally employed in the symptomatic treatment of inflammation, such as occurs with arthritis, and antirheumatics, which act in a more therapeutic fashion.

While NSAIAs can have vastly different chemical structures, most are aryl acidic molecules (though the acidic function is not essential for anti-inflammatory activity) or metabolic precursors thereof, often possessing two to three aromatic or heteroaromatic rings, either fused or linear and which are often nonplanar; the presence of a halogen or isostere atom or group usually enhances activity. Nonsteroidal anti-inflammatory agents are generally categorized into the following groups: 1) salicylates, which are derivatives of salicylic acid and include agents such as aspirin; 2) 5-pyrazolone derivatives, most of which are 3,5-pyrazolidinedione derivatives and include agents such as phenylbutazone; 3) fenamates and isosteres, which are either n-arylanthranilic or 2-aminonicotinic acid derivatives, which include such agents as meclofenmate sodium; 4) oxicams, which are mostly N-heterocyclic carboxamides of 4-hydroxy-2H-1,2-benzothiazine 1,1-dioxide, and include such agents as piroxicam; 5) other acidic compounds, such as aminobenzoic acid salts (e.g. aminobenzoate potassium), pyrocathecol derivatives (e.g. nepitrin) and the sulfonanilide derivative, nimesulide; and 6) nonacidic heterocyclic compounds, such as indazole derivatives.

The more commonly employed NSAIAs, however, are those in the category known as arylacetic acid compounds. Most arylacetic acid compounds share certain structural features: a carboxyl group or its equivalent, such as enolic acid, hydroxamic acid, sulfonamide, or a tetrazole moiety, separated by one carbon atom from a planar aromatic nucleus (hence making them acidic molecules). To the flat aromatic nucleus, one or more large lipophilic groups may be attached. The presence of an α-methyl substituent normally enhances potency, while an increase in size of this α-substituent usually diminishes activity.

Generally, the category known as arylacetic acid compounds is subdivided into the following subgroups: phenylacetic acid compounds, such as diclofenac sodium; phenylpropionic acid compounds, such as ibuprofen and naproxen; phenylbutyric acid compounds, such as indobufen; aryloxyalkanoic acid compounds, such as furobufen; and heteroarylacetic acid compounds, such as etodolac.

Given the importance of nonsteroidal anti-inflammatory agents, arylacetic acid compounds in particular, and of the criticality of employing the proper enantiomeric form, much effort has been made investigating methods for obtaining the desired optical configuration of these compounds. These techniques have ranged from attempts at synthesizing one of the two optical isomers in pure form in the first instance, to tailoring the more traditional methods of enantiomer separation to meet this particular need.

While asymmetric synthesis would theoretically reduce or eliminate the need for complex stereospecific separations, these synthetic techniques have met with limited commercial success in general applications, and have had even less success with respect to nonsteroidal anti-inflammatory agents. Stereochemical isolation and purification of these compounds have thus far relied upon chromatographic separation techniques.

Of the separation techniques in this regard, most have required derivatization of the particular NSAIA involved with some techniques even employing a chiral derivatizing agent so as to form diastereomers. However, these derivatization-dependent methods introduce increased time and cost factors into the separation and, even more importantly, introduce the possibility of error into the separation process, which now requires further steps and reactions to achieve resolution, which itself may prove to be ultimately less effective.

Procedures which require derivatization of NSAIAs with chiral reagents in order to obtain diastereomers are particularly problem prone, given that the rate of reaction of the chiral reagent with individual enantiomers may be different thus leading to a ratio of diastereomers which does not reflect the initial ratio of analyte enantiomers. Further, these procedures require scrupulous maintenance of the enantiomeric purity of the chiral reagent and avoidance of partial racemization of the analyte and chiral reagent during the course of the derivatization procedure. Lastly, the diastereomeric product ultimately obtained may give non-identical detection results, thus requiring additional validation steps.

Accordingly, to avoid these drawbacks, efforts have been made to obtain direct chromatographic separation of underivatized NSAIA enantiomers. However, these efforts have failed to be generally applicable to the entire class of NSAIAs, and have failed to be even generally applicable to any category of NSAIAs, such as the arylacetic acid category, which includes naproxen and other profen-type agents. For example, Hermansson and Eriksson in "Direct Liquid Chromatographic Resolution of Acidic Drugs Using Chiral α-1-Acid Glycoprotein Column (Enantiopac®), *J. Liq. Chromatogr.*, 9, 621 (1986) report a chromatographic separation factor ($\alpha$) of greater than 4 for underivatized naproxen using an α-1-acid glycoprotein chiral stationary phase and an achiral ion pairing reagent. However, the separation of enantiomers using a protein-derived stationary phase suffers from several important drawbacks which make these methods less than desirable for practical applications: First, since proteins are only available in one enantiomeric form, or antipode, elution orders cannot be reversed, which is often desirable in the analytical determination of enantiomeric purity. And, in any event, if a chiral selector is to find practical application as an enantioselective membrane transport agent, it is desirable that it be available in both enantiomeric forms. Secondly, proteins and protein-derived chiral stationary phases typically have rather low stability compared to synthetic chiral selectors, thus the lifetime of a protein selector or a chiral stationary phase derived therefrom, will not be as great as that for a synthetic selector; this is especially true where elevated temperatures, extremes of pH or organic solvents are involved. Finally, owing to the extremely low concentration of binding sites on the protein, preparative scale resolutions are not feasible.

Other efforts in this regard include that reported by Petterson and Gioeli in "Improved Resolution of Enantiomers of Naproxen by the Simultaneous Use of a Chiral Stationary Phase and a Chiral Additive in the Mobile Phase", *J. Chromatogr.*, 435, 225 (1988) in which underivatized enantiomers of naproxen were separated on a quinidine-based chiral stationary phase using quinine as a mobile phase additive. Separation, however, was marginal, with $\alpha = 1.18$, and poor band shape was exhibited, hence making this technique impractical for preparative purposes.

Thus there continues to be a pressing need for a process of separating enantiomers of NSAIAs, especially those categorized as arylacetic acid compounds, which does not require derivatization and which is not protein-based and which can provide a high degree of resolution and is generally applicable at least across an entire category of NSAIAs.

SUMMARY OF THE INVENTION

The present invention overcomes the inadequacies attendant enantiomeric separation techniques known heretofore for nonsteroidal anti-inflammatory agents. The present invention is directed to a chiral selector which can enantioselectively complex with underivatized nonsteroidal anti-inflammatory agents, particularly those classified as arylacetic acid compounds and hence provide a process for the efficient separation of the enantiomers of these compounds.

The chiral selector of the present invention is a compound having the formula

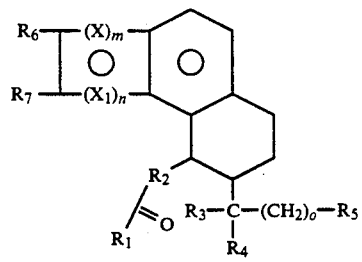

wherein
$R_1$ is

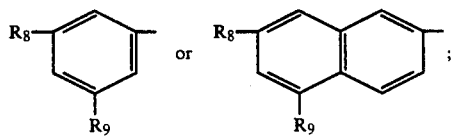

$R_2$ is O, S or NH;
$R_3$ and $R_4$ are each independently hydrogen or lower alkyl;
$R_5$ is hydrogen or $CH=CH_2$;
$R_6$ and $R_7$ are each independently hydrogen or lower alkyl or $R_6$ and $R_7$ are attached to form a 6 member aromatic ring;
X is O, S, NH or CH;
$X_1$ is O, S, NH or CH;
m is 0 or 1;
n is 0 or 1;
$R_8$ and $R_9$ are each independently $NO_2$, $N(R_{10})_3^+$ CN, $COOR_{11}$, $SO_3H$ or $COR_{12}$, wherein $R_{10}$, $R_{11}$ and $R_{12}$ are each independently hydrogen or lower alkyl; and
o is 0 or an integer from 1 to 12, said compound being an R or an S enantiomer or a mixture of R and S enantiomers.

In one embodiment of the subject invention, the chiral selector is employed in a process of separating enantiomers of a nonsteroidal anti-inflammatory agent having a first and second optical configuration, wherein said nonsteroidal anti-inflammatory agent has the formula

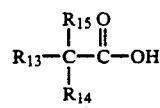

wherein
$R_{13}$ is aryl or a nitrogen, sulfur or oxygen containing heterocyclic moiety either of which may be unsubstituted or substituted with lower alkyl, lower alkoxy, aryl, aryloxy, aroyl, alkanoyl or halogen, and
$R_{14}$ and $R_{15}$ are each independently hydrogen or lower alkyl,
with a chiral selector having the formula described hereinbefore, said chiral selector being an R or S enantiomer under conditions effective to form a complex between an enantiomer of said non-steroidal anti-inflammatory agent having said first optical configuration and an enantiomer of said chiral selector; and recovering the non-complexed enantiomer of said non-steroidal anti-inflamatory agent having said second optical configuration.

In another embodiment of the present invention, the chiral selector is employed in a process of separating enantiomers of various amines, alcohol-derivatives, sulfoxides and epoxides, respectively.

The present invention is also directed to an apparatus utilizing the chiral selector. Apparatuses in this regard include liquid chromatographic columns, enantioselective membrane transport devices and liquid-liquid partitioning devices, such as countercurrent chromatographic devices.

DETAILED DESCRIPTION OF THE INVENTION

The present invention relates in one embodiment to a process for the enantiomeric separation of nonsteroidal anti-inflammatory agents, particularly those agents categorized generally as arylacetic acid compounds and more particularly those groups known as phenylpropionic acid compounds and heteroarylacetic acid compounds. The present invention further relates to a chiral selector compound having a certain structure, the use of which achieves the enantiomeric separation. Significantly, in the practice of the invention, no derivatization of the enantiomers is required prior to effecting separation, although derivatization may be employed without detriment.

The process of the invention has especial utility in separating enantiomers of underivatized arylacetic acid compounds. This class of nonsteroidal anti-inflammatory agents=may be identified by the general formula:

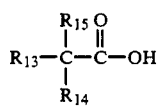

wherein $R_{13}$ is an aryl or a nitrogen, sulfur or oxygen containing heterocyclic moiety, either of which may be unsubstituted or substituted with lower alkyl, lower alkoxy, aryl, akoxyaryl, aralkyl, aryloxy, aroyl, alkanoyl, aralkanoyl or halogen, and $R_{14}$ and $R_{15}$ are each independently hydrogen or lower alkyl.

These compounds are of the R of S optical configuration and when prepared are normally produced in racenic form, thus making enantiomeric separation a necessity for practical purposes.

Among the preferred arylacetic acid compounds which may be enantiomerically separated by the process of the present invention are those generally in the subgroup known as phenylpropionic acid compounds and heteroarylacetic acid compounds.

Representative compounds of the phenylpropionic acid subgroup include: alminoprofen, benoxaprofen, carprofen, cicloprofen, cinaproxen, cliprofen, dexindoprofen, esflurbiprofen, fenclorac, fenoprofen, fenoprofen calcium, flunoxaprofen, fluprofen, flurbiprofen, frabuprofen, furaprofen, furcloprofen, hexaprofen, ibufenac, ibuprofen, ibuprofen aluminum, ibuproxam, indoprofen, isoprofen, ketoprofen, lisiprofen, lobuprofen, loxoprofen, mexoprofen, miroprofen, naproxen, naproxen sodium, naproxol, piketoprofen, pimaprofen, pineprofen, pirprofen, pranoprofen, protizinic acid rosmarinic acid, suprofen, tazeprofen, tetriprofen, ximoprofen and zoliprofen.

Representative compounds of heteroarylacetic acid subgroup include: acemetacin, anirolac, bensuldazic acid, bufezolac, cinmetacin, clidanac, clometacin, clopirac delmetacin, duometacin, eltenac, etodolac, fenclozic acid, fentiazac, glucametacin, indomethacin, indomethacin sodium trihydrate, isofezoluc, ketorolac, lonazolac, calcium niometacin, orpanoxin, oxametacin, oxaprozin, pinetacin pirazolac prodolic acid, proglumetacin, sermetacin, sulindac talmetacin, tianafac, tiaprofenic acid, tioxaprofen, tolmetin, tolmetin sodium, zidometacin and zomepirac sodium.

The structures of the more preferred compounds of these groups to which the present process has particular utility are given, in Table 1, below:

TABLE 1

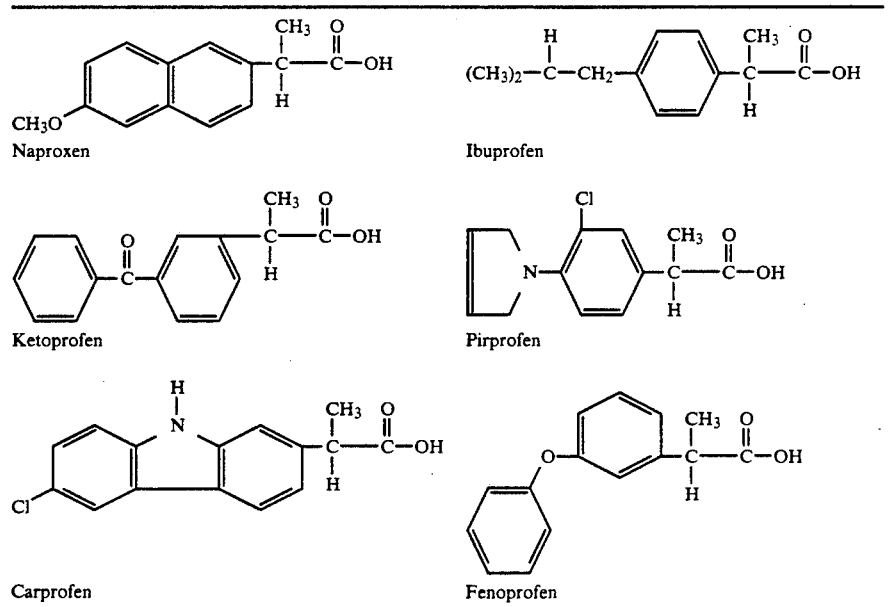

TABLE 1-continued

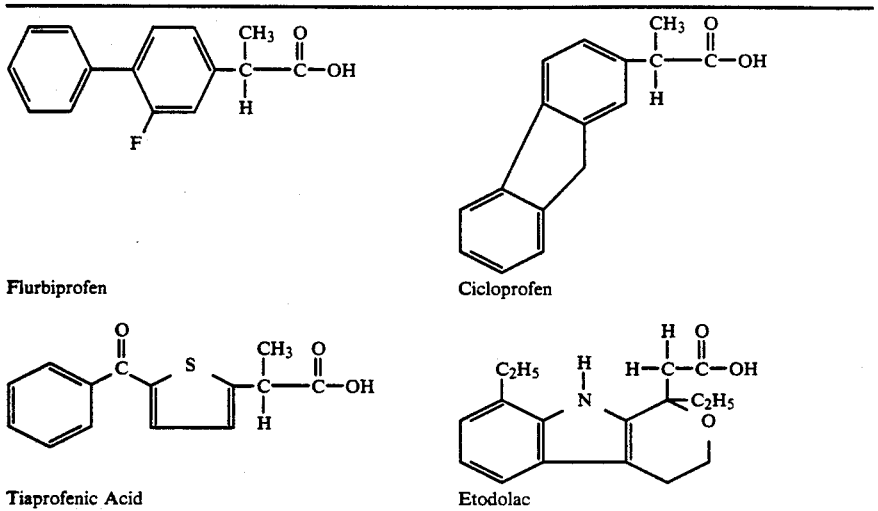

Flurbiprofen

Cicloprofen

Tiaprofenic Acid

Etodolac

The present process is most utile in performing enantiomeric separation on naproxen.

The substituents in the formulas related herein are described as follows:

As employed herein, the lower alkyl groups, singly or in combination with other groups, contain up to 6 carbon atoms which may be in the normal or branched configuration, including methyl, ethyl, propyl, isopropyl, butyl, isobutyl, t-butyl, amyl, pentyl, hexyl and the like. The preferred alkyl groups contain 1 to 3 carbon atoms.

The aryl groups are aromatic rings containing from 6 to 14 carbon atoms. Examples of aryl groups include phenyl, α-naphthyl and β-naphthyl.

The alkoxyaryl groups, singly or in combination with other groups, contain up to 16 carbon atoms, with each alkoxy group containing up to 6 carbon atoms which may be in the normal or branched configuration, and each aryl group containing from 4 to 10 carbon atoms. Preferably, each alkoxy group contains to 1 to 3 carbon atoms, and each aryl group contains 4 to 6 carbon atoms.

The aralkyl groups, singly or in combination with other groups, contain up to 16 carbon atoms with each aryl group containing from 6 to 10 carbon atoms and each alkyl group containing up to 6 carbon atoms which may be in the normal or branched configuration. Preferably, each aryl group contains 6 carbon atoms and each alkyl group contains 1 to 3 carbon atoms.

The aryloxy groups, singly or in combination with other groups contain from 6 to 10 carbon atoms. Preferably, each aryl group contains 6 carbon atoms.

The aroyl groups, singly or in combination with other groups, contain from 7 to 11 carbon atoms. Preferably, the aryl group contains 6 carbon atoms.

The alkanoyl groups, singly or in combination with other groups, contain up to 7 carbon atoms. Preferably, the alkyl groups contain 1 to 3 carbon atoms.

The aralkanoyl groups, singly or in combination with other groups, contain up to 17 carbon atoms, with each aryl group containing from 6 to 10 carbon atoms and each alkyl group containing up to 6 carbon atoms. Preferably, each aryl group contains 6 carbon atoms and each alkyl group contains 1 to 3 carbon atoms.

The lower alkoxy groups, singly or in combination with other groups, contain up to 6 carbon atoms which may be in the normal or branched configuration. Preferably each alkyl group contains 1 to 3 carbon atoms.

The alkaryl groups, singly or in combination with other groups, contain up to 16 carbon atoms with each alkyl group containing up to 6 carbon atoms which may be in the normal or branched configuration, and each aryl group containing from 6 to 10 carbon atoms. Preferably, each alkyl group contains 6 carbon atoms. The aralkenyl groups, singly or in combination with other groups, contain up to 30 carbon atoms, with each aryl group containing up to 10 carbon atoms and each alkenyl group containing up to 20 carbon atoms. Preferably, each aryl group contains 10 carbon atoms and each alkenyl group contains up to 15 carbon atoms.

The halogens include fluorine, chlorine, bromine and iodine. Preferred halogens include fluorine and chlorine.

As employed herein, the expression "a nitrogen, sulfur or oxygen containing heterocyclic moiety" is meant to include those heterocyclic ring systems which include at least one sulfur, nitrogen or oxygen ring atom but which may include one or several of said atoms. The expression also includes saturated and unsaturated heterocyclics as well as heteroaromatic rings. These groups contain from 10 to 15 ring atoms on the heterocyclic moiety. Representatives heterocyclics include furan, thiophene, pyrrole, pyridine, pyrazole, pyrazine, pyrimidine, pyridazine, oxazole, quinoline, isoquinoline, indole, benzothiophene, benzofuran, imidizole, benzoxazote, piperazine, tetrahydrofuran and the like.

The chiral selector of the present invention is a compound having the following formula:

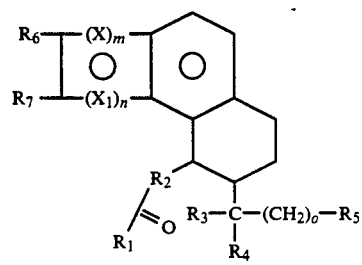

wherein

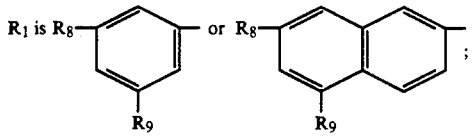

R$_2$ is O, S or NH;

R$_3$ and R$_4$ are each independently hydrogen or lower alkyl;

R$_5$ is hydrogen or CH=CH$_2$;

R$_6$ and R$_7$ are each independently hydrogen or lower alkyl or R$_6$ and R$_7$ are attached to form a 6 member aromatic ring.

X is O, S, NH or CH;

X$_1$ is O, S, NH or CH;

m is 0 or 1;

n is 0 or 1;

R$_8$ and R$_9$ are each independently NO$_2$, N(R$_{10}$)$_3^+$, CN, COOR$_{11}$, SO$_3$H or COR$_{12}$, wherein R$_{10}$, R$_{11}$ and R$_{12}$ are each independently hydrogen or lower alkyl; and o is 0 or an integer from 1 to 12, said compound being an R or an S enantiomer or a mixture of R and S enantiomers.

In the practice of the present invention, the substituents denoted above as $$R_2\overset{O}{\underset{}{\|}}R_1 \text{ and } R_3-\underset{R_4}{\overset{|}{C}}-(CH_2)_o-R_5$$

may be in the trans, or the cis position relative to one another; the cis position is preferred.

In preferred embodiments of the chiral selector of the instant invention

R$_1$ is preferably R$_8$

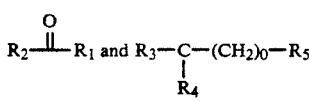

R$_2$ is preferably NH.

R$_3$ and R$_4$ are preferably each independently hydrogen or methyl, with hydrogen being more preferred.

R$_5$ is preferably CH=CH$_2$.

R$_6$ and R$_7$ are preferably attached to form a 6 member aromatic ring when X is O, S or NH, preferably O, and m is 1 and n is 0, or R$_6$ and R$_7$ are preferably attached to form a 6 member aromatic ring when X$_1$ is O, S or NH, preferably O, and m is 0 and n is 1. In a more preferred embodiment, R$_6$ and R$_7$ are hydrogen or methyl, methyl being more preferred, and X and X$_1$ are each CH and m and n are each 1.

R$_8$ and R$_9$ are preferably NO$_2$.

A particularly preferred chiral selector for effecting separation of nonsteroidal anti-inflammatory agents, particularly those classified as arylacetic acid compounds and more particularly, those in the subgroup known as phenylpropionic acid compounds and heteroarylacetic acid compounds, is the chiral selector having the formula

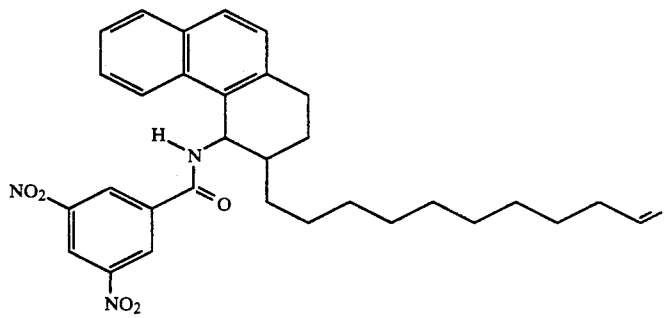

hereinafter identified as CS-10 and also known by its name 4-(3,5-dinitrobenzoyl)amino-3-(undec-10-enyl)-1,2,3,4-tetrahydrophenanthrene.

Another preferred chiral selector for effecting separation of non-steroidal anti-inflammatory agents, particularly those classified as arylacetic acid compounds and more particularly, those in the subgroup known as phenylpropionic acid compound and heteroarylacetic acid compound is the chiral selector having the formula:

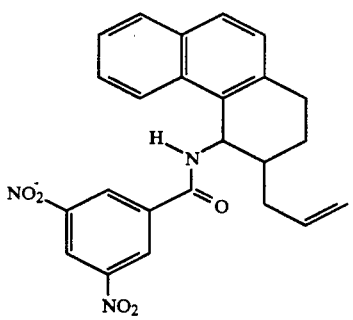

hereinafter identified as CS-2 and also known by its name 4-oxo-3-allyl-1,2,3,4-tetrahydrophenanthrene.

Still another preferred chiral selector for effecting separation of non-steroidal anti-inflammatory agents, particularly those classified as arylacetic acid compounds and more particularly those in the subgroup known as phenyl propionic acid compound and heteroarylacetic acid compounds is the chiral selector having the formula:

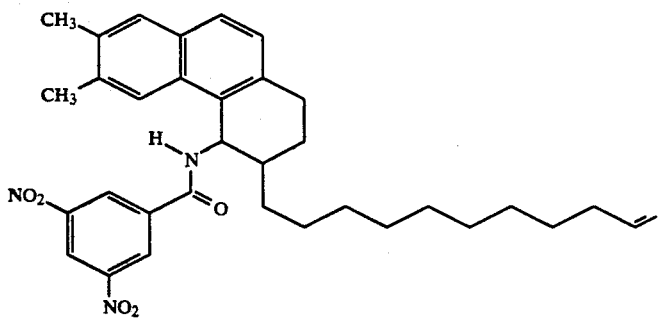

hereinafter identified as CS-8 and also known by its name 6,7-Dimethyl-4-[N-(3,5-dinitrobenzoyl)]amino-3-(10-undecenyl)-1,2,3,4-tetrahydrophenanthrene.

In another embodiment of the present invention, the chiral selector having the formula described hereinabove is employed in a process for the separation of enantiomers of amines having the general formula

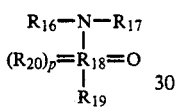

wherein $R_{16}$ and $R_{17}$ are each independently hydrogen, aralkyl, aralkenyl or $R_{16}$ and $R_{17}$ together with the N to which they are attached form a 3, 4, 5 or 6 member ring having the general formula

wherein $R_{21}$ and $R_{22}$ are each independently hydrogen, lower alkyl, aryl, alkaryl or aralkyl and q is 1, 2, 3 or 4, $R_{18}$ is C or S, $R_{19}$ is lower alkyl, aryl, alkaryl or aralkyl any of which may be unsubstituted or substituted with $NO_2$, $N(R_{23})_3$, CN, $COOR_{24}$, $SO_3H$ or $COR_{25}$ wherein $R_{23}$, $R_{24}$ and $R_{25}$ are each independently hydrogen or lower alkyl, $R_{20}$ is O and p is 1 when $R_{18}$ is S, and p is 0 when $R_{18}$ is C.

Representative amines having this formula are shown in Table 2, below:

TABLE 2

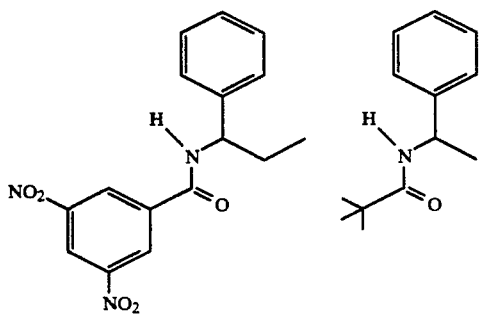

TABLE 2-continued

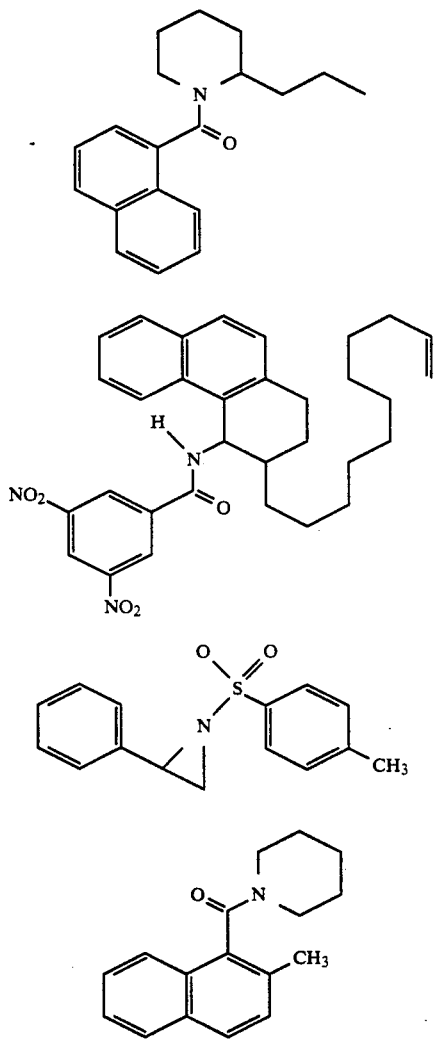

In yet another embodiment of the present invention, the chiral selector having the formula described hereinabove is employed in a process for the separation of enantiomers of alcohol derivatives having the general formula

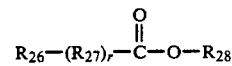

wherein $R_{26}$ is hydrogen, lower alkyl or aryl either of which may be unsubstituted or substituted with $NO_2$, $N(R_{29})_3$, CN, $COOR_{30}$, $SO_3H$ or $COr_{31}$ wherein $R_{29}$, $R_{30}$ and $R_{31}$ are each independently hydrogen or lower alkyl, $R_{27}$ is $NR_{32}$ wherein $R_{32}$ is hydrogen or lower alkyl, $R_{28}$ is lower alkyl, aryl or aralkyl and r is 0 or 1.

Representative alcohol derivatives having this formula are shown in Table 3, below:

TABLE 3

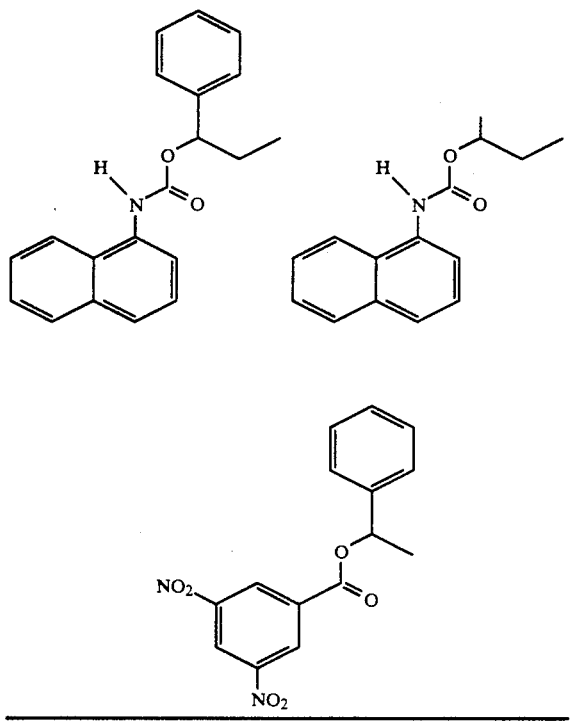

In still another embodiment of the present invention, the chiral selector having the formula described hereinabove is employed in a process for the separation of enantiomers of epoxides having the general formula

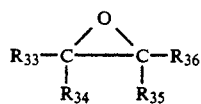

wherein $R_{33}$, $R_{34}$, $R_{35}$ and $R_{36}$ are each independently hydrogen, lower alkyl, aryl, alkaryl or aralkyl.

Representative epoxides having this formula are shown in Table 4, below

TABLE 4

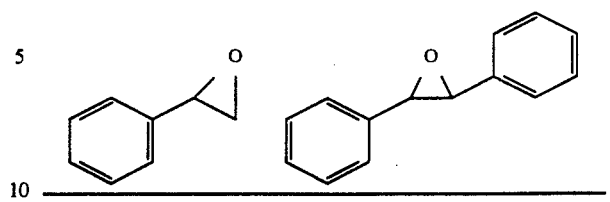

In yet still another embodiment of the present invention, the chiral selector having the formula described hereinabove is employed in a process for the separation of enantiomers of sulfoxides having the general formula

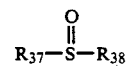

wherein $R_{37}$ and $R_{38}$ are each independently lower alkyl or an aryl or a nitrogen, sulfur or oxygen containing heterocyclic moiety, or $R_{37}$ or $R_{38}$ may together with the S to which they are attached from a 4 or 5 member ring having the formula

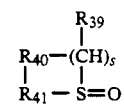

wherein $R_{39}$ is hydrogen or lower alkyl, $R_{40}$ is O or S, $R_{41}$ is aryl and s is 1 or 2.

Representative sulfoxides having this formula are shown in Table 5, below

TABLE 5

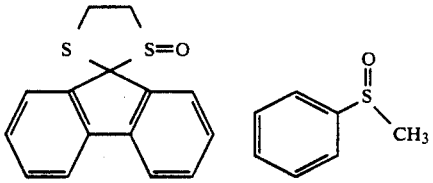

The chiral selectors of the present invention may be prepared by conventional chemical preparation techniques. For illustrative purposes, the preparation of the preferred chiral selector is described below but those skilled in the art can readily appreciate the modifications necessary to prepare other chiral selectors within the scope of the formula depicted hereinabove.

The synthetic sequence used to prepare the chiral selector of the present invention is exemplified for CS-10, as shown in Table 7, below. Those of skill in the art will appreciate that the synthetic sequence delineated hereinbelow is readily modified to provide other chiral selectors of the instant invention.

TABLE 7

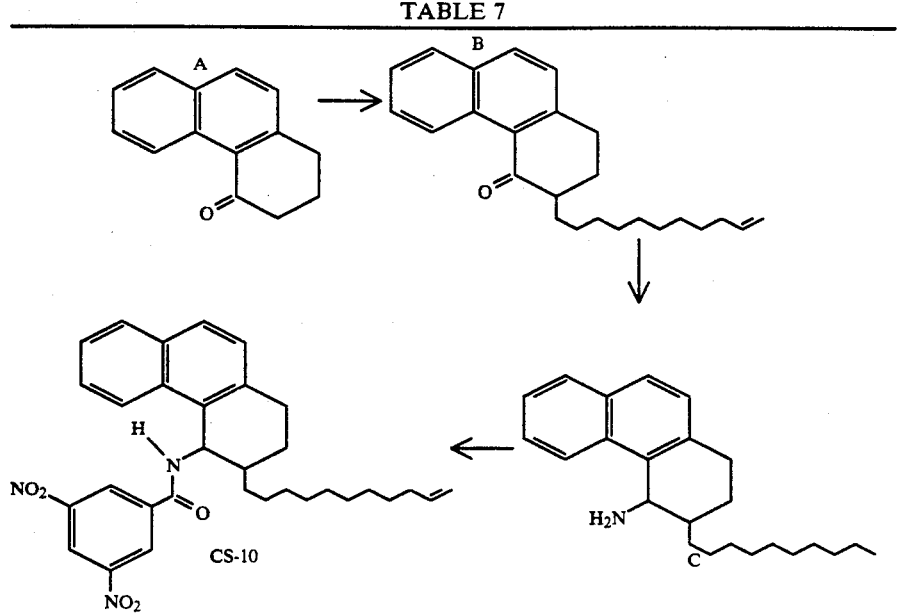

This preparation began with 4-oxo-1,2,3,4-tetrahydrophenanthrene (identified as Compound A, Table 7), as described by S roeter, G. et al. in "Uber die Hydrierung des Phenanthrens", *Ber. der. Deutschen Chem*, 62, 645, 1929. Alkylation of this phenanthrene with 11-iodoundec-1-ene was performed in refluxing benzene using potassium t-butoxide as a base. Reductive alkylation of the resulting monoalkylated ketone (identified as Compound B, Table 7), using sodium cyanoborohydride and ammonium acetate in isopropyl alcohol at 95° C. gave a mixture of cis- and trans- amines (identified as Compound C, Table 7), which were converted to the corresponding 3,5-dinitrobenzamies (identified as CS-10, Table 7), without purification. The mixture of cis- and trans- amides (about 5:1) was then separated by flash chromatography upon silica gel Enantiomeric separation was performed at this stage using a preparative version of a chiral stationary phase described by Pirkle, Deming and Burke in *Chirality*, 3:183–187 (1991) the contents of which are incorporated herein by reference; this chiral stationary phase was derived from S-N-(1-naphthyl) leucine and having the formula

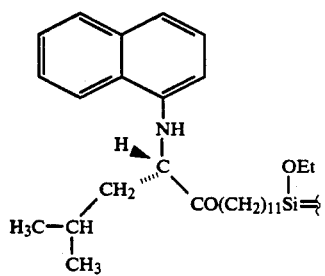

Enantiomeric separation by means of the chiral selectors of the invention may be achieved in a variety of techniques known in the art. In one embodiment, the chiral selector may form the active portion of the stationary phase in an HPLC column. In this embodiment of the present invention, the terminal W of the formula must be $CH=CH_2$ so as to permit the chiral selector to be immobilized on a support which is suitable for use in chromatographic separations. Supports in this regard include, e.g., silica and alumina In one configuration, the chiral selector is immobilized by covalently bonding it to silanized silica. Thus, for example as shown in Table 8, below, hydrosilation of enantiomerically pure CS-10 gives a silane (identified as Compound D, Table 8) which was bonded to 5μ(100Å silica gel and slurry packed into a stainless steel analytical HPL column (4.6 mm×250 mm) to give a chiral stationary phase based on CS-10 (CSP-10)).

TABLE 8

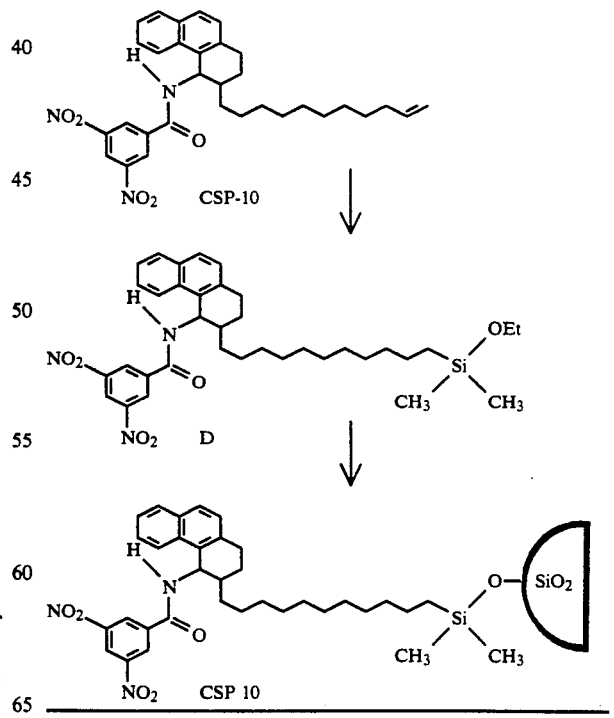

Since the chiral selectors of the invention are optically active, it is necessary to separate the chiral selectors so that either the R or the S enantiomers of the chiral selector is employed as the stationary phase in the column, depending upon which of the enantiomers to be separated is to be preferentially bound to the chiral selector.

The techniques of enantiomers separation by HPLC are known in the art. Commercially available HPLC columns employing chiral stationary phases, such as those available from Regis Chemical Company, can be employed in practicing the subject invention. See, for example, "Systematic Studies of Chiral Recognition Mechanisms", W. H. Pirkle, et al., Pages 23–25 in "Chiral Separations", Stephenson and Wilson, eds. Plenum Press, New york, 1988, the contents of which are incorporated herein by reference.

In another embodiment of the present invention, the chiral selectors of the subject invention may be employed to effect separations using semi-permeable membranes wherein the chiral selector forms part of a mobile phase Such techniques are also well known, including the use of semi-permeable membranes in the form of hollow fiber membranes In this embodiment, it is preferred that the terminal W in the formula of the chiral selector be hydrogen so as to minimize covalent bonding by the chiral selector In one particularly useful embodiment, the chiral selector forms part of a liquid membrane passing on one side of a semi-permeable barrier with enantiomers to be separated passing on the other side of the barrier. The pores of the membrane become impregnated with the liquid membrane containing the chiral selector One of the enantiomers forms a complex with the chiral selector, passes through the membrane into the moving liquid membrane and is conducted to a second location wherein disassociation takes place. This technique is disclosed in commonly assigned patent application Ser. No. 528,007, filed May 23, 1990, now U.S. Pat. No. 5,080,795, the contents of which are incorporated herein by reference.

The following examples are given to illustrate the scope of the invention. Because these examples are given for illustrative purposes only, the invention embodied therein should not be limited thereto.

EXAMPLE 1

Preparation of CS-10

Apparatus and Materials

Chromatographic analysis was performed using a Rainin HPX Rabbit pump, a Rheodyne Model 7125 injector with a 20 sample loop, a Milton Roy-LDC UV absorbance Monitor D ® fixed wavelength detector operating at 254 nm, and a Shimadzu CR1A integrating recorder.

Solvents used were HPLC grade or were distilled prior to use. (S)-naproxen was used as received from Sepracorp. Dimethylchlorosilane was obtained from Petrarch Chemicals.

Preparation of 4-(3,5-dinitrobenzoyl)amino-3-(undec-10-enyl)-1,2,3,4-tetrahydrophenanthrene (CS-10) (see Table 7, supra)

Synthesis of 11-Iodoundec-1-ene

A solution of 93.5 g of undec-10-en-1-ol and 100 mL of triethylamine in 500 mL of dry dichloromethane was treated with 68.7 g of methanesulfonyl chloride at 0° C. according to the method reported by Crossland, R. K., et al. in "A Facile Synthesis of Methanesulfonate Esters" *J. Org. Chem.*, 35, 3195 (1970). The crude reaction mixture was then evaporated and partitioned between water and ether. The ether layer was collected, washed with water, then dried over anhydrous magnesium sulfate. Filtration and evaporation gave 142 g of a colorless oil which was immediately converted to the iodo compound. A solution of 137 g sodium iodide and 1.2 g dicyclohexano-18-crown-6 in 150 mL of water was stirred with 64 g of the crude mesylate on a steam bath for 5 h. The reaction mixture was then extracted several times with ether, the combined ether fractions were washed with water, then dried over anhydrous magnesium sulfate. Filtration and evaporation gave the crude iodo compound as an oil which was vacuum distilled to give 62.8 g (90% yield) of almost colorless oil, b.p. 118°–122° C./4.5 mn Hg, lit. 104° C./2 mm Hg. This compound was used in the synthesis of the alkylated ketone or described hereinbelow.

Synthesis of the alkylated ketone (Compound B, Table 7)

In a 1 L three-necked round bottom flask equipped with a Teflon paddle stirrer, nitrogen inlet, and a Dean-Stark trap, 500 mL of benzene was dried by azeotropic water removal. Solid potassium tert.-butoxide, 12.3 g, was added at 50° C. giving a clear solution. A solution of 8.9 g of 4-O-1,2,3,4-tetrahydrophenanthrene, as described by Scroeter, G. et al. in "Uber die Hydrierung des Phenanthrens", *Ber. der Deutschen Chem.*, 62, 645 (1929) (Compound A, Table 7) and 14 g of 11-iodoundec-1-ene (synthesized according to the method described above) in 100 mL of dry benzene was added at 40° C., causing the reaction mixture to darken somewhat. Stirring at 40° C. was continued for 45 min., then the reaction mixture was heated at reflux for 2 h. During this period, approximately 400 mL of benzene was allowed to distill off. Cooling the reaction mixture followed by extraction with water, drying the organic phase with anhydrous magnesium sulfate, filtration, and evaporation gave 19 g of a dark oil which was purified by flash chromatography on silica using 1:1 dichloromethane/hexane as eluent to give 9.9 g of alkylated ketone (Compound B, Table 2) (63% yield).

Reductive amination to form 4-amino-3-(undec-10-enyl)-1,2,3,4-tetrahydrophenanthrene (Compound C, Table 7)

In a 250 mL thick-walled Parr bottle was mixed 5 g of alkylated ketone (Compound B, Table 7) as synthesized according to the method described above, 6 g sodium cyanoborohydride, 30 g ammonium acetate, and 100 mL 2-propanol. After securely closing the bottle with a rubber stopper, the contents were heated to 90°–95° C. for 24 h by immersion of the bottle in a steam bath. A safety shield was placed in front of the bottle, which had also been wrapped in cloth. After cooling and evaporation the crude product was partitioned between ether and water, the ether layer was dried with anhydrous magnesium sulfate, filtered, and evaporated to give 5.9 g of an oil which showed no traces of alkylated ketone (Compound B, Table 7) by thin layer chromatography (TLC). The crude amine was carried on to the next step without further purification.

Synthesis of 4-(3,5-dinitrobenzoyl) amino-3-(undec-10-enyl)-1,2,3,4-tetrahydrophenanthrene (CS-10)

The crude amine synthesized according to the method described above was dissolved in 150 mL dichloromethane and stirred with excess saturated sodium hydrogen carbonate solution. 3,5-Dinitrobenzoyl chloride, 5 g, dissolved in the minimum amount of dichloromethane was then added, and the resulting two-phase mixture was stirred vigorously for 1 h. The organic layer was then dried, concentrated to approximately 20 mL volume, and purified by flash chromatography on silica with dichloromethane as eluent. Both cis and trans isomers of CS-10 were obtained in about a 5:1 ratio, respectively. Separation of the diastereomers was incomplete by flash chromatography; nevertheless, pooling of the pure fractions containing the desired cis diastereomer gave 2.2 g of CS-10 (a 28% yield from Compound B, Table 7).

Separation of the enantiomers of CS-10

Separation of the enantiomers of CS-10 was performed with a chiral stationary phase derived from S-N-(1-naphthyl) leucine which was prepared as described by Pirkle, Deming and Burke in *Chirality*, 3:183-187 (1991) the contents of which are incorporated herein by reference.

Separation of the enantiomers of CS-10 was performed using this chiral stationary phase derived from S-N-(1-naphthyl)leucine at a flow rate of 40 mL/min of 10% 2-propanol in hexane with continuous redistillation and recycling of mobile phase. Two bands were obtained 1 g samples of the nearly pure fast-eluting enantiomers of CS-10 having the (R,R) configuration were isolated, as were samples of the slow-eluting enantiomers of CS-10 having the (S,S) configuration.

Chiral Stationary Phase of CS-10

Hydrosilation of CS-10

The fast eluting enantiomers (R,R) of CS-10 was dissolved, 1 g, in a mixture of 10 mL of dimethylchlorosilane (Petrarch Chemicals) and 10 mL of dichloromethane. Chloroplatinic acid (about 10 mg), dissolved in a minimum amount of 2-propanol, was then added, and the reaction mixture was heated at reflux under a nitrogen atmosphere. After 2 h, a quenched (as described below) aliquot of the reaction mixture was subjected to TLC analysis, showing the disappearance of starting material. The reaction mixture was evaporated to dryness on a rotary evaporator to give the crude chlorosilane as a dark oil. Residual dimethylchlorosilane was removed by three successive additions and evaporations of small portions of dichloromethane. A solution of 5 mL triethylamine, 5 mL absolute ethanol, and 5 mL diethyl ether was then added to the crude chlorosilane and the mixture was stirred at room temperature under nitrogen atmosphere for 30 minutes The mixture was then filtered to remove precipitated triethylamine hydrochloride. The filtrate was then used without further purification in the preparation of CSP-10.

Bonding to silica to form CSP-10

The filtrate from the hydrosilation of CS-10, as described above, containing the crude ethoxysilane (Compound D, Table 8) was added to 5 g Regis Rexchrom silica (5μ, 100Å) which had been previously dried by azeotropic water removal with benzene. Dimethylformamide, (1 mL) was then added, and the slurry was carefully evaporated to dryness under reduced pressure. The moist slurry was then rocked in a Kügelrohr oven at 90°-95° C./1 mm Hg for 24 hours. The silica gel was then washed extensively with ethanol and then methanol, slurried in methanol and packed into a 4.6 mm×250 mm stainless steel HPLC column to afford CSP-10. Excess silica gel removed from the column packer reservoir was submitted for elemental analysis (C 7.27%; H 0.95%; N 0.71%) to reveal a loading of 0.18 mMole chiral selector per gram of stationary phase. After preliminary analysis, the residual silanols on the stationary phase were endcapped by passing a solution of 2 mL of hexamethyldisilazane (HMDS) in 50 mL dichloromethane through the methylene chloride equilibrated column at a flow rate of 1 mL/min.

Analytes and their separation

All chromatographic experiments were carried out at a nominal flow rate of 2.00 mL/min. Column void time was measured by injection of tri-t-butylbenzene, a presumed unretained solute. Variable temperature data were collected with the mobile phase reservoir and pump at ambient temperature, and with the column immersed in a large constant temperature bath. About two feet of 0.009 in ID stainless steel tubing was used to connect the column to the injector and was wrapped around the inverted column as a heat exchanger to thermally equilibrate the mobile phase prior to column entry Mobile phases consisting of alkanes and lower molecular weight alcohols, and, optionally, containing lower molecular weight carboxylic acids and/or lower molecular weight amines were used to permit separation of enantiomers of naproxen and other analytes.

Enantiomeric mixtures of naproxen and selected α-arylacetic acid compounds of interest were subjected to separation with HPLC columns to compare the effectiveness of CS-10 of the present invention when forming the active part of the stationary phase (CSP-10) in the column.

Two mobile phases were separately utilized: Mobile Phase A, which comprised 5% 2-propanol and 0.1% acetic acid in hexane, and Mobile Phase B, which comprised 20% 2-propanol, 0.1% acetic acid and 0.1% triethylamine in hexane.

Chromatographic data for naproxen and nine other α-aryl acetic acid compounds were obtained using the (R,R) configuration of CS-10 of the invention. The results are presented below in Table 9.

TABLE 9

Separation of Underivatized naproxen and other arylacetic acid compounds on CSP-10

| Analyte | Mobile Phase A | | Mobile Phase B | |
|---|---|---|---|---|
| | $k'_1$ | α | $k'_1$ | α |
| naproxen | 3.31 | 1.97 | 5.86 | 2.20 |
| ibuprofen | 0.27 | 1.22 | 0.75 | 1.20 |
| ketoprofen | 3.11 | 1.05 | 5.08 | 1.22 |
| flurbiprofen | 0.64 | 1.30 | 2.05 | 1.31 |
| pirprofen | 1.85 | 1.27 | 3.35 | 1.33 |
| fenoprofen | 0.57 | 1.40 | 1.46 | 1.43 |
| cicloprofen | 2.53 | 1.60 | 4.00 | 1.67 |
| carprofen | 2.20 | 1.40 | 6.30 | 1.42 |
| tiaprofenic acid | 6.40 | >1.00 | 13.45 | 1.12 |
| etodolac | 0.87 | 1.23 | — | — |

$k'_1$ = the capacity factor for the first eluted enantiomer using the indicated mobile phases and flow rates. The detector was operating at 254 nm.
α = the chromatographic separation factor From these data, it can be seen that CSP-10 achieved a high degree of chromatographic separation (u) of the underivatized analytes Using Mobile Phase A, all of the analytes, except ketoprofen and tiaprofenic acid, were baseline resolved under these chromatographic conditions. In mobile phases containing a small amount of triethylamine in addition to acetic acid (Mobile Phase B), baseline resolution of all the analytes was easily obtained Chromatographic data for the amines, alcohol derivatives, epoxides and sulfoxides shown in Tables 2, 3, 4 and 5, respectively, were obtained using the (R,R) configuration of CS-10 of the invention using either of Mobile Phase A or Mobile Phase B, or a third Mobile Phase C, which comprised 2% 2-propanol in hexane; all other conditions were as described above. The resolution results are shown in Tables 10, 11, 12, and 13, below.

TABLE 10

Separation of Amines on CSP-10

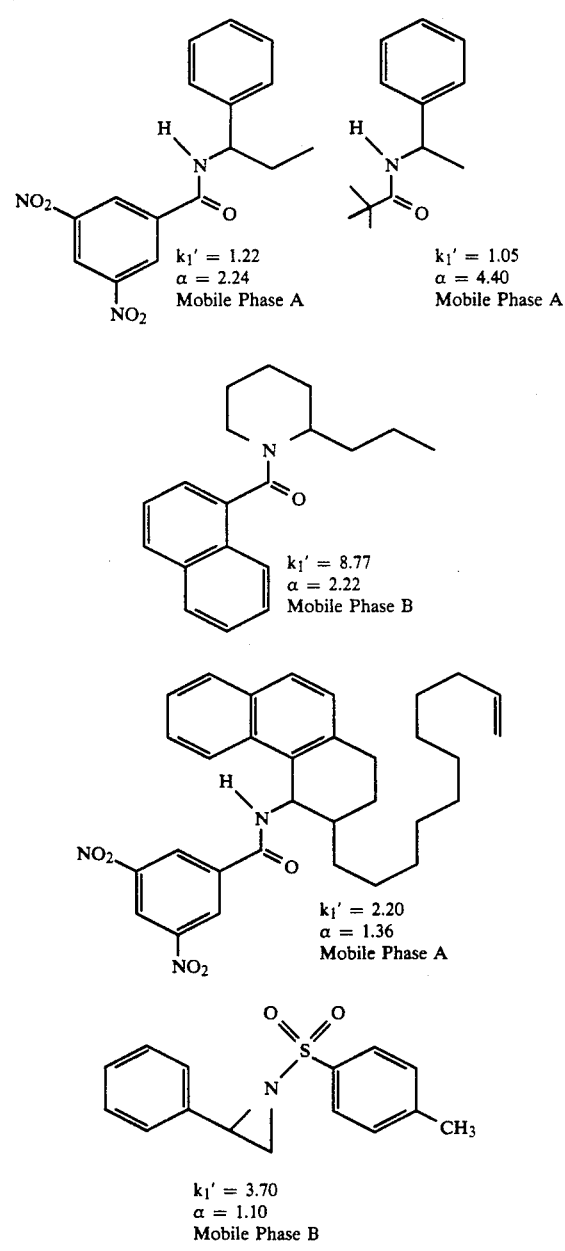

TABLE 10-continued

Separation of Amines on CSP-10

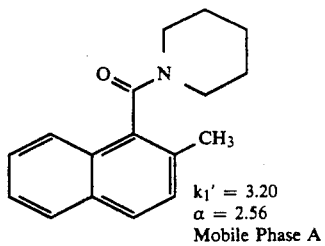

$k_1' = 3.20$
$\alpha = 2.56$
Mobile Phase A

TABLE 11

Separation of Alcohol Derivatives on CSP-10

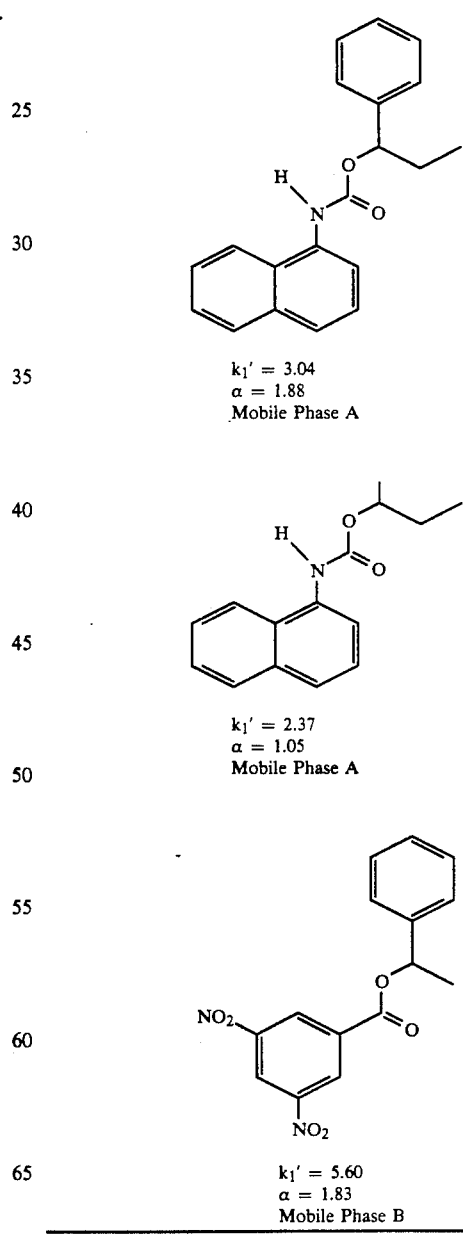

TABLE 12

Separation of Epoxides on CSP-10

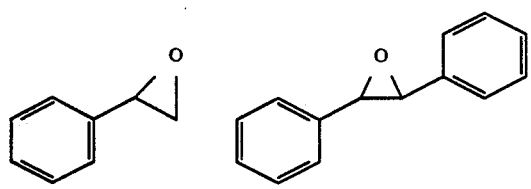

| $k_1' = 0.73$ | $k_1' = 0.48$ |
| $\alpha = 1.22$ | $\alpha = 2.33$ |
| Mobile Phase C | Mobile Phase B |

TABLE 13

Separation of Sulfoxides on CSP-10

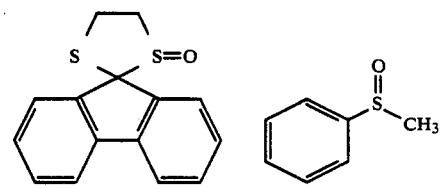

| $k_1' = 2.00$ | $k_1' = 8.12$ |
| $\alpha = 2.10$ | $\alpha = 1.18$ |
| Mobile Phase A | Mobile Phase B |

As seen from these data, high degrees of resolution, as measured by the chromatographic separation factor, are obtained with the chiral selector of the present invention, as embodied on CSP-10.

EXAMPLE 2

Preparation of CS-2

The synthetic sequence used to prepare CS-2 is shown in Table 14, below.

TABLE 14

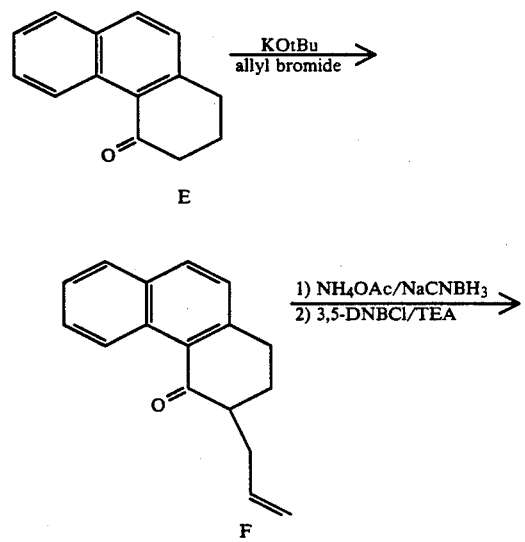

TABLE 14-continued

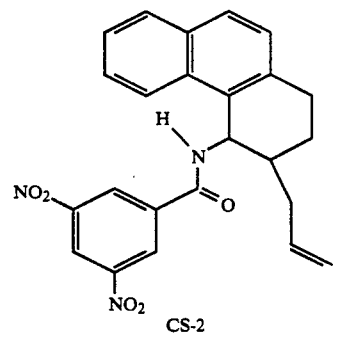

CS-2

Apparatus and Materials

Chromatographic analysis was performed using a Altex model 100A pump, a Rheodyne model 7125 injector with a 20 μl sample loop, a Linear UVIS 200 variable wavelength absorbance monitor, set at 254 nm, and a Hewlett-Packard HP 3394A integrating recorder. All $^1$H NMR spectra were recorded on a Varian XL 200 FT NMR spectrometer.

All reagents were of pharmaceutical or reagent grade and were used without further purification. Solvents used were HPLC grade or distilled prior to use. Dimethylchlorosilane was obtained from Petrarch Systems, Bristol, Pa. Rexchrom 5μ 100 Å silica gel was obtained from Regis Chemical Co., Morton Grove, Ill.

Preparation of Racemic 4-oxo-3-allyl-1,2,3,4-tetrahydrophenanthrene (CS-2)

Transformation of the ketone, 4 oxo-1,2,3,4-tetrahydrophenanthrene (Compound E, Table 14), which ketone has been reported by Premasager, V. et al. in *J. Org. Chem.*, 46, pp. 2974 (1981) to CS-2 followed the method in Example 1 for CS-10.

Alkylation of the ketone (Compound E, Table 14) with allyl bromide gave Compound F (Table 14). Reductive amination of Compound F (Table 14) followed by acylation with 3,5-dinitrobenzoyl chloride gave CS-2. $^1$H NMR (200 M Hz, CDCl$_3$)δ: 1.60 (m,1H), 2.10 (m,3H), 2.65 (m,1H), 3.19 (m,2H), 5.12 (m,2H), 6.00 (m,1H), 6.18 (dd,1H, J = 10 Hz and 3 Hz), 6.34 (d,1H, J = 10 Hz), 7.29 (d,1H), 7.45 (m,2H), 7.79 (m,2H), 8.05 (d,1H, J = 8.4 Hz), 8.88 (d,2H, J = 2.3 Hz).

Separation of the Enantiomers of CS-2

The enantiomers of CS-2 were chromatographically separated on a 25 mm×900 mm column containing a chiral stationary phase derived from (S)-N-(1-naphthyl)leucine chiral stationary phase which was prepared as described by Pirkle, Deming and Burke in *Chirality*, 3:183–187 (1991) the contents of which are incorporated herein by reference Separation of the enantiomers of CS-2 was performed using this chiral stationary phase derived from (S)-N-(1-naphthyl) leucine at a flow rate of 40 ml/min. of 10% 2-propanol in hexane with continuous redistillation and recycling of mobile phase Two bands were obtained Samples of the nearly pure fast-eluting enantiomers of CS-2 having the (R,R) configuration were isolated, as were samples of the slow-eluting enantiomers of CS-2 having the (S,S) configuration (0.85 g).

Chiral Stationary Phase of CS-2

The synthetic sequence used to prepare to chiral stationary phase of CS-2 is shown in Table 15, below.

TABLE 15

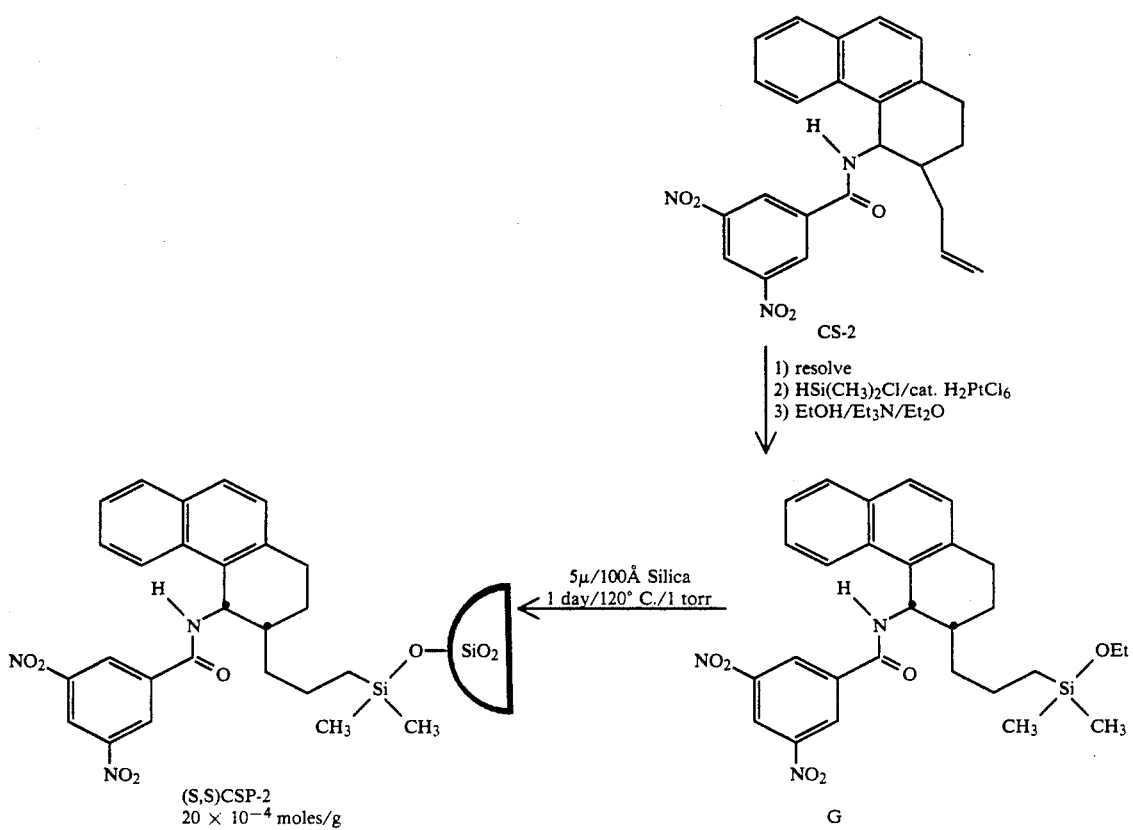

Hydrosilation of CS-2

The second eluting enantiomers of CS-2 (0.85 g) assigned the (S,S) absolute configuration by a combination of HPLC, NMR, and x-ray crystallographic evidence was dissolved in a mixture of 10 mL of dimethylchlorosilane and 10 mL of dichloromethane. Chloroplatinic acid (about 5 mg) dissolved in a minimum amount of 2-propanol was then added and the reaction mixture was heated at reflux under a nitrogen atmosphere. After 1 h, a quenched aliquot of the reaction mixture showed (by TLC analysis) no remaining starting material. The reaction mixture was evaporated to dryness on a dark oil. Residual dimethylchlorosilane was removed by three successive additions and evaporations of small portions of dichloromethane. A mixture of 5 mL of triethylamine, 5 mL of absolute ethanol, and 5 mL of diethyl ether was then added to the crude chlorosilane and the mixture was stirred at room temperature under a nitrogen atmosphere for 30 minutes. The mixture was filtered to remove triethylamine hydrochloride and evaporated to afford the crude ethoxyorganosilane which was purified by flash chromatography on silica using 5% ethanol/dichloromethane as eluent to give 0.93 g ethoxyorganosilane (Compound G, Table 15) (88% yield). $^1$H NMR (200M Hz, CDCl$_3$)$\delta$: 0.09 (s,6H), 0.62 (m,2H), 1.18 (t,3H), 1.60 (m,5H), 2.05 (m,2H), 3.10 (m,2H), 3.68 (q,2H), 6.11 (dd,1H), 6.33 (d,1H), 7.29 (d,1H), 7.45 (m,2H), 7.79 (m,2H), 8.10 (d,1H), 8.85 (d,2H), 9.10 (t,1H).

Bonding to Silica to Form CSP-2

A solution of 0.93 g ethoxyorganosilane (Compound G, Table 15) dissolved in 1 mL of dimethylformamide was added to a dichloromethane slurry of 5 g of Regis Rexchorm silica (5μ, 100 Å) which had been previously dried by azeotropic water removal with benzene. The slurry was carefully evaporated to dryness under reduced pressure, then heated at 120° C. /1 torr for 24h. The silica gel was washed extensively with ethanol and then methanol, slurried in methanol and packed into a 4.6 mm×250 mm stainless steel HPLC column. Elemental analysis of residual packing (C 4.95%; H 0.61%; N 0.56%) showed a loading of 2.0×10$^{-4}$ moles of chiral selector per gram of stationary phase. The residual silanol groups were endcapped by passing a solution of 2 mL of hexamethyldisilazane in 50 mL dichloromethane through the dichloromethane equilibrated column at a flow rate of 1 mL/min.

Analytes and their Separation

All chromatographic experiments were carried out at a nominal flow rate of 2.00 mL/min. unless otherwise indicated. Column void time was measured by injection of tri-t-butylbenzene, a presumed unretained solute as reported by Pirkle, et al. in *J. Liq. Chromatogr*, 14, 1, (1991) incorporated herein by reference. $^1$H NMR chemical shifts were reported in ppm ($\delta$) relative to tetramethylsilane. Variable temperature data were collected with the mobile phase reservoir and pump at ambient temperature, and with the column immersed in a large constant temperature bath. About two feet of 0.009 in ID stainless steel tubing was used to connect the column to the injector and was wrapped around the inverted column as a heat exchanger to thermally equilibrate the mobile phase prior to column entry.

Enantiomeric mixtures of naproxen and selected α-arylacetic acid compounds of interest were subjected to separation with HPLC columns to compare the effectiveness of CS-2 of the present invention, when it forms the active part of the stationary phase of the column. The separation afforded by CS-2 under these circumstances was compared with CS-10 of the present invention as prepared according to Example 1; each separately formed the active part of the stationary phase (denoted as CSP-2 and CSP-10) in the respective columns.

The mobile phase utilized comprised 20% 2-propanol in hexane containing 1 g/L ammonium acetate Chromatographic data for naproxen and seven other α-arylacetic acid compounds were obtained using the S,S configurations of CS-2 and CS-10 of the invention. The results are presented below in Table 16

TABLE 16

Separation of Underivatized Naproxen and Other Arylacetic Acid Compounds on CSP-10 and CSP-2

| | CSP-10 | | | CSP-2 | | |
|---|---|---|---|---|---|---|
| Compound | $k'_1$ | $k'_2$ | α | $k'_1$ | $k'_2$ | α |
| Naproxen | 3.96 | 8.95 | 2.26 | 1.71 | 5.01 | 2.93 |
| Ibuprofen | 0.94 | 1.05 | 1.12 | 0.19 | 0.28 | 1.47 |
| Ketoprofen | 4.53 | 5.03 | 1.11 | 1.39 | 1.79 | 1.29 |
| Flurbiprofen | 1.63 | 1.94 | 1.19 | 0.37 | 0.59 | 1.59 |
| Pirprofen | 2.53 | 3.49 | 1.38 | 0.85 | 1.54 | 1.81 |
| Fenoprofen | 1.48 | 1.81 | 1.22 | 0.38 | 0.61 | 2.50 |
| Cicloprofen | 3.03 | 5.18 | 1.71 | 1.16 | 2.50 | 2.15 |
| Tiaprofenic Acid | 6.15 | 6.70 | 1.09 | 2.02 | 2.48 | 1.23 |

Conditions: Flow rate = 2.0 mL/min.; mobile phase = 20% 2-propanol in hexane containing 1 g/L ammonium acetate;
$k'_1$ = capacity factor for first eluted enantiomer.
$k'_2$ = capacity factor for second eluted enantiomer.
α = the chromatographic separation factor.

From these data, it can be seen that CSP-2 achieved an even higher degree of chromatographic separation (α) of the underivatized analytes than CSP-10, with an α for CSP-2 of nearly three (2.93, at room temperature) being obtained for naproxen. Analyte capacity factors (k's), as apparent in Table 16, were consistently less on the short-tethered CSP-2 as opposed to the longer tethered CSP-10. This was especially true for the less retained enantiomer.

EXAMPLE 3

Preparation of CS-8

Apparatus and Materials

Melting points were taken on a Buchi apparatus and are uncorrected. $^1$H NMR spectra were recorded on a Varian XL-200 spectrometer in CDCl$_3$ and were referenced to tetramethylsilane or residual CHCl$_3$ (7.24 ppm). IR spectra were taken on a IBM IR/32 FTIR spectrometer. High resolution mass spectra were obtained on a Varian 731 mass spectrometer at SCS Mass Spectrometry Laboratory, University of Illinois at Urbana-Champaign.

Chromatography was performed with a HPLC system which consists of an Anspec-Bischoff model 2200 HPLC pump, a Rheodyne 7125 injector with 20 μl sample loop, a Milton Roy UV Monitor ™ D fixed wavelength detector operating at 254 nm and a Kipp & Zonen BD 41 recorder.

Preparation of 3-(6,7-Dimethyl-1 and 2-naphthoyl)propanoic Acid

Anhydrous AlCl$_3$ (19 g, 0.14 mole) was added to 200 ml of CH$_2$Cl$_2$ with stirring at 0° C. To the stirred heterogeneous solution was added succinic anhydride (12 g, 0.12 mole) and then 2,3-dimethylnaphthalene (15.6 g, 0.1 mole) at 0° C. After stirring overnight at room temperature, 200 ml of 1 N HCl, 10 ml of 12 N HCL and then 300 ml of ethylacetate were added to the reaction mixture. The whole mixture was shaken vigorously in a separatory funnel and then the two phases (organic phase:upper phase) were separated. The organic phase was extracted with 1 N NaOH. The NaOH solution was washed with ether (200 ml) and then acidified with 12 N HCl to afford yellow solid material in the aqueous phase. The whole mixture was extracted with ethylacetate. The ethylacetate solution was dried over anhydrous Na$_2$SO$_4$ and then concentrated to afford yellow solid material This solid material was crystallized from ethylacetate. The first crop 6.58 g, 25.7% yield) was found to be pure 3-(6,7,-dimethyl-2-naphthoyl)-propanoic acid (β-isomer) and the second crop (6.85 g, 26.8% yield) was 3-(6,7-dimethyl-1-naphthoyl)-propanoic acid (α-isomer) by NMR. β-Isomer: yellow needle crystal, mp 183.0°-185.0° C., $^1$H NMR (CDCl$_3$)δ 2.45 (s,6H), 2.87 (t, J=6.7 Hz,2H), 3.45 (t, J=6.7 Hz,2H), 7.63 (s,1H), 7.71 (s,1H), 7.77 (d, J=8.5 Hz,1H), 7.95 (d, J=8.5 Hz,1H), 8.41 (s,1H), IR (KBr) cm$^{-1}$ 3300–2800, 1698, 1678, 1610, 1597, Anal. calcd. for C$_{16}$H$_{16}$O$_3$: C, 74.98; H, 6.29. Found: C, 74.63; H, 6.17.

α-Isomer: yellowish solid, mp 162.0°-163.0° C., $^1$H NMR (CDCl$_3$)δ 2.42 (s,3H), 2.44 (S,3H), 2.89 (t, J=6.3 Hz, 2H), 3.40 (t, J=6.3 Hz,2H), 7.37–7.44 (m,1H), 7.62 (s,1H), 7.87 (d, J=6.8 Hz,1H), 7.89 (d, J=8.3 Hz,1H), 8.43 (s,1H), IR (KBr) cm$^{-1}$ 3330–2800, 1698, 1669, 1580, 1500, Anal. Calcd. for C$_{16}$H$_{16}$O$_3$: C, 74.98; H, 6.29. Found: C, 75.22; H, 6.18.

Preparation of 4-(6,7-Dimethyl-2-naphthyl)butanoic acid

The β-isomer, 3-(6,7-Dimethyl-2-naphthoyl)-propanoic acid (6.58 g, 0.026 mole) was dissolved into 200 ml of THF in a hydrogenation pressure bottle. To the solution was carefully added 30% Pd/C (700 mg). The whole mixture was shaken for 15 hrs under H$_2$ (40 psi) at room temperature. After releasing pressure, Pd/C was removed by passing the THF solution through the celite pad. The solution was concentrated to afford 4-(6,7-Dimethyl-2-naphthyl)butanoic acid as a gray solid material (6.21 g, 0.026 mole, 100% yield). mp 141.0°-142.0° C., $^1$H NMR (CDCl$_3$)δ 1.98–2.12 (m,2H), 2.36–2.41 (m,8H), 2.81 (t, J=7.4 Hz,2H), 7.22 (d, J=8.3 Hz,1H), 7.49–7.55 (m,3H), 7.65 (d, J=8.3 Hz,1H), IR (KBr) cm$^{-1}$ 3700–3450,2920,1698, Anal. Calcd for C$_{16}$H$_{18}$O$_2$: C, 79.31; H, 7.49. Found: C, 79.28; H, 7.49.

Preparation of 6,7-Dimethyl-4-oxo-1,2,3,4-tetrahydrophenanthrene 4-(6,7-Dimethyl-2-naphthyl)butanoic acid (6.21 g, 0.026 mole) was added to 40 ml of CH$_3$SO$_3$H. The mixture was heated to 90° C. until all solid material disappeared (about 30 min.). The mixture was poured into ice and then extracted twice with ethylacetate. Combined ethylacetate solution was dried over anhydrous Na$_2$SO$_4$ and then concentrated. After flash chromatography on silica gel, 6,7-Dimethyl-4-oxo-1,2,3,4-tetrahydrophenanthrene was obtained as a pale yellow solid material (4.96 g, 0.022 mole, 85% yield). mp 114.0°-115.0° C., $^1$H NMR (CDCl$_3$)δ 2.12-2.20 (m,2H), 2.41 (s,3H), 2.47 (s,3H), 2.77 (t, J=6.4 Hz,2H), 3.09 (t, J=6.4 Hz,2H), 7.21 (d, J=8.3 Hz,1H), 7.54 (s,1H), 7.31 (d, J=8.3 Hz,1H), 9.20 (s,1H), IR (KBr) cm$^{-1}$ 2930, 1669, 1590, 1510, Anal. Calcd. for C$_{16}$H$_{16}$O: C, 85.67; H, 7.19. Found: C, 86.00; H, 7.18.

Preparation of 6,7-Dimethyl-4-oxo-3-(10-undecenyl)-1,2,3,4-tetrahydrophenanthrene t-BuOK (3.6 g, 0.032 mole) was dissolved in 250 ml of dry benzene at 40°-50° C. To the stirred solution was added 6,7-Dimethyl-4-oxo-1,2,3,4-tetrahydrophenanthrene (3.6 g, 0.016 mole) in 50 ml of dry benzene and then, 10-undecenyl iodide (4.58 g, 0.016 mole) at 30° C. under N$_2$. The mixture was heated to 60° C. for 2.5 hr under N$_2$. After cooling the reaction mixture to room temperature, water was added. The whole mixture was extracted twice with diethylether. The combined diethylether solution was dried over anhydrous MgSO$_4$. and then concentrated. Flash column chromatography of the residue on silica gel afforded 6,7-Dimethyl-4-oxo-3-(10-undecenyl)-1,2,3,4-tetrahydrophenanthrene as a sticky brown solid (2.36 g, 0.0063 mole, 39% yield) as a desired product, and unreacted 6,7-Dimethyl-4-oxo-1,2,3,4-tetrahydrophenanthrene (1.70 g, 47% recovered). $^1$H NMR (CDCl$_3$)δ 1.29-1.62 (m,14H), 1.86-2.08 (m,4H), 2.21-2.35 (m,2H), 2.40 (s,3H), 2.46 (s,3H), 2.52-2.63 (m,1H), 3.07-3.13 (m,2H), 4.90-5.04 (m,2H), 5.75-5.89 (m,1H), 7.17 (d, J=8.2 Hz,1H), 7.53 (s,1H), 7.77 (d, J=8.2 Hz,1H), 9.10 (s,1H), IR (KBr) cm$^{-1}$ 2920, 2850, 1669, 1600, exact (EI) mass. calcd. for C$_{27}$H$_{36}$O: 376.2766, Found: 376.2766.

Preparation of 6,7-Dimethyl-4-[N-(3,5-dinitrobenzoyl)]amino-3-(10-undecenyl)-1,2,3,4-tetrahydrophenanthrene (CS-8)

6,7-Dimethyl-4-oxo-(10-undecenyl)-1,2,3,4-tetrahydrophenanthrene (6.6 g, 0.018 mole) was dissolved in 300 ml of methyl alcohol in a pressure bottle. To the solution was added 60 g of ammonium acetate and 10 g of sodiumcyanoborohydride. The whole mixture was heated to 100°-105° C. for 48 hrs in the closed pressure bottle. After cooling down the reaction mixture to room temperature, the pressure bottle was opened carefully. After adding 200 ml of 1N HCl to the reaction mixture (which resulted in the generation of HCN gas), methyl alcohol was removed from the reaction mixture using a rotary evaporator. The residual aqueous solution was made basic (pH>10) by adding KOH pellets, and was then extracted twice with diethyl ether. The organic phase was dried over anhydrous Na$_2$SO$_4$ and then concentrated to afford a viscous oily material. This viscous oily material was dissolved in 100 ml of dry CH$_2$Cl$_2$. To the stirred solution was added 3,5-dinitrobenzoyl chloride (5.52 g, 0.028 mole) and triethylamine (4.2 ml, 0.030 mole). After stirring for 15 min. at room temperature, the reaction mixture was washed with 0.5N HCl, 0.5 N NaOH, and then brine solution. The organic solution was dried over anhydrous Na$_2$SO$_4$ and then concentrated. The residue was purified by flash column chromatography on silica gel to afford a yellowish solid material (7.66 g, 0.0134 mole, 76% yield). This solid material was found to be the mixture of cis and trans isomers of CS-8 (the ratio of cis:trans=4.9:1) by analysis on a chiral HPLC column.

Separation of the Enantiomers of CS-8

By chromatographing the mixture of cis and trans isomers of CS-8 on a (S)-N-(1-naphthyl)leucine chiral stationary phase packed into a MPLC column, which chiral stationary phase is described by Pirkle, Deming and Burke in *Chirality*, 3:183-187 (1991) the contents of which are incorporated herein by reference, 2.68 g of enantiomerically pure cis CS-8, i.e., (cis)-6,7-Dimethyl-4-[N-(3,5-dinitrobenzoyl)]amino-3-(10-undecenyl)-1,2,3,4-tetrahydrophenanthrene, (last eluted enantiomer) was obtained, as were samples of the trans form of CS-8 (the first eluted enantiomer). Physical data for cis CS-8, obtained as a yellowish solid, were as follows mp 181°-182° C., $^1$H NMR (CDCl$_3$)δ 1.19-1.39 (m,14H), 1.42-1.77 (m,3H), 1.96-2.07 (m,4H), 2.36 (s,3H), 2.40 (s,3H), 3.03-3.10 (m,2H), 4.89-5.03 (m,2H), 5.74-5.88 (m,1H), 6.08 (dd, J=9.2 Hz, J=2.8 Hz,1H), 6.20 (d, J=9.2 Hz,1H), 7.16 (d, J=8.2 Hz,1H), 7.52 (s,1H), 7.61 (d, J=8.2 Hz,1H), 7.85 (s,1H), 8.84 (d, J=1.7 Hz,2H), 9.08 (t, J=1.7 Hz,1H), IR (KBr) CM$^{-1}$ 3440, 2920, 2850, 1680, 1650, 1540, 1500, exact (EI) mass. calcd. for C$_{34}$H$_{41}$N$_3$O$_5$: 571.3046, Found: 571.3046, [α]$_D^{20}$-126.2(c 091, CH$_2$Cl$_2$).

Chiral Stationary Phase of (cis)-CS-8

Hydrosilation of (cis)-CS-8

Preparation of (Cis)-6,7-Dimethyl-4-[N-3,5-Dinitrobenzoyl)]amino-3-(10-dimethylethoxysilylundecyl)-1,2,3,4-tetrahydrophenanthrene (Cis)-CS-8 (1.75 g, 3.06×10$^{-3}$ mole) was dissolved in 20 ml of methylene chloride. To the solution were added 20 ml of dimethylchlorosilane and 0.2 ml of a H$_2$PtCl$_6$ solution (72 mg of H$_2$PtCl$_6$ in 5 ml of isopropyl alcohol). This mixture was refluxed under nitrogen with stirring. After refluxing for 1.5 hr., excess dimethylchlorosilane and methylene chloride were removed by simple distillation followed by application of high vacuum. The oily residue was dissolved in 30 ml of dry methylene chloride and then the mixture of ethyl alcohol and triethylamine (3 ml, 1:1 mixture) was added. After stirring for 10 min. at room temperature, all solvent was removed and the residue was purified by flash column chromatography on silica gel to afford (cis)-6,7-Dimethyl-4-[N-(3,5-Dinitrobenzoyl)]amino-3-(10-dimethylethoxysilylundecyl-1,2,3,4-tetrahydrophenanthrene as a yellowish dense liquid (0.7 g, 34% yield). $^1$H NMR (CDCl$_3$)δ 0.09 (s,6H), 0.54–0.62 (m,2H), 1.18 (t, J=7.0 Hz,3H), 1.22-1.44 (broad m, 18H). 1.50-1.80 (m,3H). 1.95-2.13 (m,2H), 2.34 (s,3H), 2.40 (s,3H), 3.05-3.08 (m,2H), 3.65 (q, J=7.0 Hz,2H), 6.09 (dd, J=9.2 Hz, J=3.2 Hz,1H), 6.25 (d, J=9.2 Hz,1H), 7.13 (d, J=8.3 Hz,1H), 7.47 (s,1H), 7.56 (d, J=8.3 Hz,1H), 7.85 (s,1H), 8.82 (d, J=2.2 Hz,2H), 9.00 (t, J=2.2 Hz,1H), IR (KBr) cm$^{-1}$ 3350, 2910, 2850, 1630, 1550 1510, exact (EI) mass. calcd, for C$_{38}$H$_{53}$N$_3$O$_6$Si: 675.3704, Found: 675.3706, [α]D$^{20}$−82.3 (c 1.00, CH$_2$Cl$_2$).

Bonding to Silica to form CSP-8

A 200 ml flask equipped with a Dean-Stark trap and a condenser was charged with 4.5 g of 5 μm Rexchrom silica gel and 60 ml of benzene. After heating at reflux until water was completely removed, enantiomerically pure (cis)-6,7-Dimethyl-4-[N-(3,5-Dinitrobenzoyl)-]amino-3-(10-dimethylethoxysilylundecyl)-1,2,3,4-tetrahydrophenanthrene (700 mg) in 10 ml of dry benzene was added and heated to reflux again to remove water. After removal of water, 1 ml of dimethylformamide was added and then the solvent was carefully evaporated to dryness under reduced pressure. The whole mixture was heated to 100°-105° C. for 2 hrs. in a Kügelrohr oven under vacuum. The silica gel was washed sequentially with benzene, methanol, ethylacetate, methylene chloride, hexane and pentane and then dried at 80° C. under vacuum. Anal Found: C 7.55%, H 0.93%, N 0.55%, calcd. loading: 0.16 mmoles of chiral selector per gram of stationary phase based on C. The modified silica gel was slurried in methanol and packed into a 4.6 mm×250 mm stainless steel column using a conventional method. The residual silanols were endcapped by eluting a solution of 2 ml of hexamethyldisilazane in 50 ml of methylene chloride through the CSP column previously charged with methylene chloride.

Analytes and their Separation

All chromatographic experiments were carried out at a nominal flow rate of 2.00 mL/min. unless otherwise indicated. Column void time was measured by injection of tri-t-butylbenzene, a presumed unretained solute, in the manner described by Pirkle, et al. in *J. Liq. Chromatogr.*, 14, 1, (1991), incorporated herein by reference.

Mobile phases consisting of alkanes and lower molecular weight alcohols and, optionally containing lower molecular weight carboxylic acids and/or lower molecular weight amines were used to permit separation of enantiomers of naproxen and other analytes.

Enantiomeric mixtures of naproxen and selected α-arylacetic acid compound of interests and various analogues thereof were subjected to separation with HPLC columns to compare the effectiveness of CS-8 of the present invention when forming the active part of the stationary phase (CSP-8) in the column. The chromatographic data was obtained using the cis configuration of CS-8 of the invention. The results are presented below in Tables 17, 18, 19 and 20, which tables separately identify the mobile phases utilized.

TABLE 17

Separation of underivatized naproxen and other 2-arylpropionic acids and analogues thereof on CSP-8

| 2-Arylpropionic Acid | $k_1'$ | $k_2'$ | α | Mobile Phase | Elution Order |
|---|---|---|---|---|---|
| Naproxen | 4.97 | 11.33 | 2.28 | D | S |
| Ibuprofen | 0.69 | 0.83 | 1.20 | E | |
| Flurbiprofen | 1.47 | 2.07 | 1.41 | E | |
| Fenoprofen | 1.00 | 1.89 | 1.89 | E | |
| Carprofen | 8.17 | 10.33 | 1.31 | D | |
| Pirprofen | 4.50 | 7.11 | 1.58 | E | |
| Cicloprofen | 3.29 | 5.59 | 1.70 | D | |
| Tiaprofenic acid | 4.29 | 4.71 | 1.10 | D | |
| Etodolac | 3.33 | 4.46 | 1.34 | E | |
| 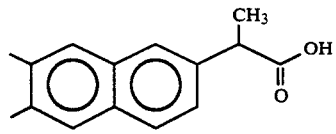 | 5.88 | 19.20 | 3.27 | D | |
| 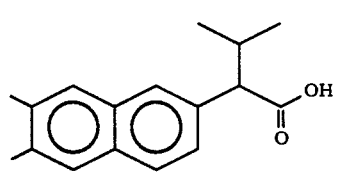 | 4.33 | 12.60 | 2.91 | D | |
| 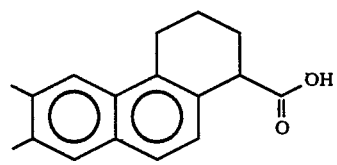 | 3.51 | 12.07 | 3.44 | D | |
| 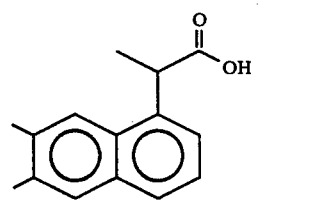 | 2.20 | 2.33 | 1.06 | D | |

TABLE 17-continued

Separation of underivatized naproxen and other
2-arylpropionic acids and analogues thereof on CSP-8

| 2-Arylpropionic Acid | $k_1'$ | $k_2'$ | α | Mobile Phase | Elution Order |
|---|---|---|---|---|---|
| (structure) | 0.71 | 1.17 | 1.66 | D | |

Mobile Phase D was 0.1% acetic acid and 5% isopropyl alcohol in hexane. Mobile Phase E was 0.1% acetic acid and 2% isopropyl alcohol in hexane. Flow rate was 2 ml/min.

$k_1'$ = The capacity factor for the first eluted enantiomer using the indicated mobile phases and flow rates.

$k_2'$ = The capacity factor for the second eluted enantiomer using the indicated mobile and flow rates.

α = The chromatographic separation factor.

From the date of Table 17, it can be seen that CSP-8 achieved a high degree of chromatographic separation (α) of the underivatized analytes, especially naproxen.

Chromatographic data for the separation of underivatized naproxen and other arylacetic acid compounds using the cis-configuration of CSP-8 and Mobile Phase F which comprises 20% isopropyl alcohol in hexane containing 1.00 ml acetic acid/L (0.1%) and 1 ml of triethylamine/L (0.1%), is shown in Table 18 below.

TABLE 18

Separation of Underivatized Naproxen and Other Arylacetic Acids on CSP-8 using Mobile Phase F

| Solutes | $k_1'$ | $k_2'$ | α |
|---|---|---|---|
| Naproxen | 5.36 | 15.04 | 2.81 |
| Ibuprofen | 0.43 | 0.60 | 1.40 |
| Ketoprofen | 3.00 | 4.26 | 1.42 |
| Flurbiprofen | 1.36 | 2.44 | 1.80 |
| Fenoprofen | 0.87 | 1.94 | 2.23 |
| Carprofen | 3.39 | 4.71 | 1.39 |
| Pirprofen | 2.73 | 5.26 | 1.93 |
| Cicloprofen | 4.00 | 8.39 | 2.10 |
| Tiaprofenic acid | 7.94 | 10.36 | 1.30 |
| Etodolac | 2.13 | 2.40 | 1.13 |
| 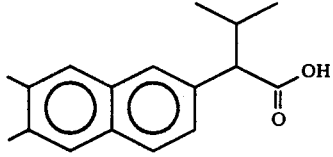 | 4.47 | 14.59 | 3.26 |

$k_1'$ = The capacity factor for the first eluted enantiomer using the indicated mobile phase and flow rate.
$k_2'$ = The capacity factor for the second eluted enantiomer using the indicated mobile phase and flow rate.
α = The chromatographic separation factor.

As can be seen from the data elucidated in Table 18 high levels of chromatographic separation were obtained. Indeed, as compared to that elucidated in Table 17 (using CSP-8 and Mobile Phases D and E), an increase in chromatographic separation (α) for naproxen, ibuprofen and etodolac was obtained using CSP-8 in conjunction with Mobile Phase F.

Chromatographic data for the separation of enantiomers of 3,5-Dinitrobenzamides of 1-(p-methoxyphenyl)alkylamines on CSP-8 (cis configuration) using Mobile Phase G which comprised 30% isopropyl alcohol in hexane, is shown in Table 19, below. Flow rate was 20 ml/min.

TABLE 19

Separation of Enantiomers of 3,5-Dinitrobenzamides of 1-(p-methoxyphenyl)alkylamines on CSP-8 using Mobil Phase G CH₃O—⟨phenyl⟩—CH—NH—DNB
             |
             R

| | $k_1'$ | $k_2'$ | α |
|---|---|---|---|
| R = CH₃ | 15.07 | 36.26 | 2.41 |
| R = CH₂CH₃ | 10.99 | 24.86 | 2.26 |
| R = (CH₂)₂CH₃ | 11.69 | 24.41 | 2.09 |
| R = (CH₂)₃CH₃ | 11.01 | 24.86 | 2.26 |
| R = (CH₂)₄CH₃ | 10.71 | 23.29 | 2.17 |
| R = (CH₂)₅CH₃ | 10.20 | 22.86 | 2.24 |
| R = (CH₂)₆CH₃ | 9.84 | 22.57 | 2.29 |
| R = (CH₂)₇CH₃ | 9.40 | 22.03 | 2.34 |
| R = (CH₂)₈CH₃ | 8.90 | 21.50 | 2.42 |
| R = (CH₂)₉CH₃ | 7.57 | 18.69 | 2.47 |
| R = (CH₂)₁₀CH₃ | 7.30 | 18.43 | 2.52 |
| R = (CH₂)₁₂CH₃ | 6.93 | 18.41 | 2.66 |
| R = (CH₂)₁₄CH₃ | 6.29 | 17.40 | 2.77 |
| R = (CH₂)₁₆CH₃ | 5.64 | 16.29 | 2.89 |

$k_1'$ = The capacity factor for the first eluted enantiomer using the indicated mobile phase and flow rate.
$k_2'$ = The capacity factor for the second eluted enantiomer using the indicated mobile phase and flow rate.
α = The chromatographic separation factor.

As seen from the data of Table 19, high levels of chromatographic separation (α) was achieved for all the 3,5-dinitrobenzamides of 1-(p-methoxyphenyl)alkylamines that were studied using CSP-8 and Mobile Phase G.

Chromatographic data for the separation of a variety of other racemic compounds on CSP-8 (cis configuration) are shown in Table 20 below. The mobile phases utilized for the experiments reported in Table 20 comprised the percentage of isopropyl alcohol indicated in Table 20, in hexane. Flow rate was 2 ml/min.

Table 20

Separation of a Variety of Racemic Compounds on CSP-8 using the Mobile Phase having the Percentage of Isopropyl Alcohol indicated in Hexane

| Solutes | $k_1'$ | $k_2'$ | $\alpha$ | % isopropyl alcohol in hexane |
|---|---|---|---|---|
| Ph-S(=O)-Me | 7.56 | 10.14 | 1.34 | 10% |
| p-Tolyl-S(=O)-Et | 5.60 | 8.21 | 1.47 | 10% |
| NC-C6H3(cyclic ketal with t-Bu) | 3.43 | 10.43 | 3.04 | 5% |
| trans-stilbene oxide | 0.43 | 1.37 | 3.20 | 20% |
| trans-(4-chlorophenyl)phenyl oxirane | 0.47 | 1.17 | 2.48 | 20% |
| 1-phenylethyl N-(3,5-dinitrophenyl)carbamate | 2.79 | 6.89 | 2.47 | 20% |
| 7-chloro-3-benzyl-5-phenyl-benzodiazepinone | 0.57 | 0.90 | 1.58 | 20% |
| H3C-CH(O-β-Naph)-C(=O)-OCH2CH3 | 1.14 | 1.83 | 1.60 | 20% |
| H3C-CH(O-α-Naph)-C(=O)-OCH2CH3 | 1.14 | 1.86 | 1.63 | 20% |
| Ph-β-lactone with allyl-(CH2)8 | 0.67 | 1.20 | 1.79 | 20% |
| Ph-C(=O)-CH(OH)-Ph | 0.99 | 2.29 | 2.32 | 20% |

Table 20-continued

Separation of a Variety of Racemic Compounds on CSP-8 using the Mobile Phase having the Percentage of Isopropyl Alcohol indicated in Hexane

| Solutes | $k_1'$ | $k_2'$ | $\alpha$ | % isopropyl alcohol in hexane |
|---|---|---|---|---|
| 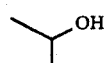 | 0.99 | 1.29 | 1.30 | 20% |
| 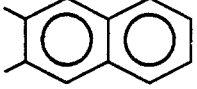 | 2.06 | 2.91 | 1.42 | 20% |
| 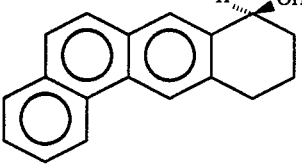 | 1.44 | 1.90 | 1.32 | 20% |
| 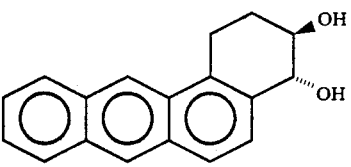 | 8.57 | 23.43 | 2.73 | 20% |
| 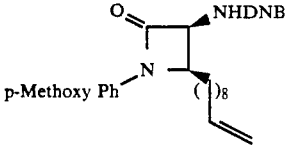 | 3.13 | 3.63 | 1.16 | 10% |
| 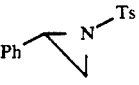 | 3.70 | 7.91 | 2.14 | 20% |
| 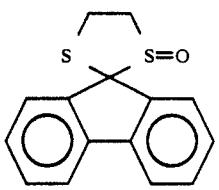 | 1.14 | 2.00 | 1.75 | 10% |

$k_1'$ = The capacity factor for the first eluted enantiomer using the mobile phase and flow rate indicated.
$k_2'$ = The capacity factor for the second eluted enantiomer using the mobile phase and flow rate indicated.
$\alpha$ = The chromatographic separation factor.

As apparent from Table 20, CS-8 of the present invention, forming the active portion of chiral stationary phase CSP-8, showed high degrees of chromatographic separation ($\alpha$) over a wide range of different racemates.

What is claimed is:

1. A method of producing a stationary phase for a liquid chromatography column which comprises immobilizing an R or an S enantiomer of a compound having the formula:

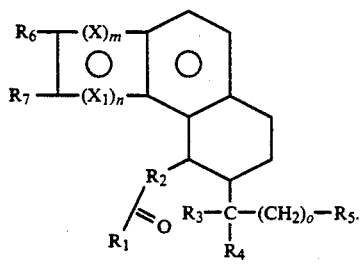

wherein
R₁ is

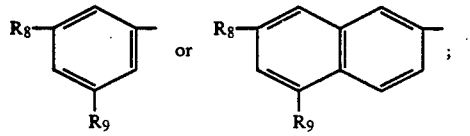

R₂ is O, S or NH;
R₃ and R₄ are each independently hydrogen or lower alkyl;
R₅ is hydrogen or CH=CH₂;
R₆ and R₇ are each independently hydrogen, lower alkyl or R₆ and R₇ are attached to form a 6 member aromatic ring;
X is O, S, NH or CH;
X₁ is O, S, NH or CH;
m is 0 or 1;
n is 0 or 1; and
R₈ and R₉ are each independently $NO_2$, $N(R_{10})_3^+$, CN, $COOR_{11}$, $SO_3H$ or $COR_{12}$, wherein $R_{10}$, $R_{11}$ and $R_{12}$ are each independently hydrogen or lower alkyl; and
o is 0 or an integer from 1 to 12;
on a support effective for use in chromatographic separation.

2. A method of producing a stationary phase for a liquid chromatography column which comprises immobilizing an R or an S enantiomer of a compound having the formula:

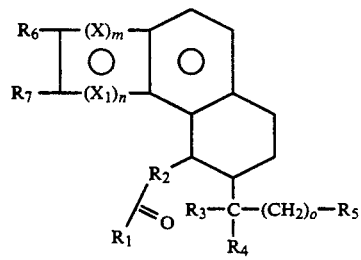

wherein
R₁ is

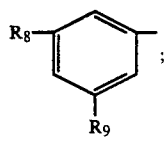

and
R₂ is NH;
R₃ and R₄ are each hydrogen;
R₅ is CH=CH₂;
R₆ and R₇ are each hydrogen;
X and X₁ are each CH;
m and n are each 1;
R₈ and R₉ are each NO₂, wherein $R_{10}$, $R_{11}$ and $R_{12}$ are each independently hydrogen or methyl; and
o is 8;
on a support effective for use in chromatographic separation.

3. A method of producing a stationary phase for a liquid chromatography column which comprises immobilizing an R or S enantiomer of a compound having the formula:

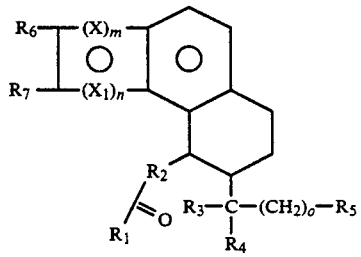

wherein
R₁ is

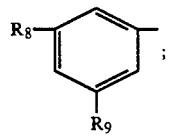

and
R₂ is NH;
R₃ and R₄ are each hydrogen;
R₅ is CH=CH₂;
R₆ and R₇ are each independently methyl;
X and X₁ are each CH;
m and n are each 1;
R₈ and R₉ are each NO₂, wherein $R_{10}$, $R_{11}$ and $R_{12}$ are each independently hydrogen or methyl; and
and o is 8;
on a support effective for use in chromatographic separation.

4. A method of producing a stationary phase for a liquid chromatography column which comprises immobilizing an R or an S enantiomer of a compound having the formula:

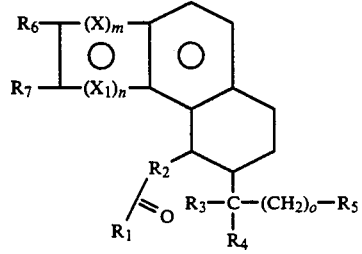

wherein
R₁ is

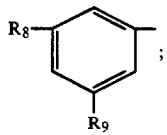
and
R$_2$ is NH;
R$_3$ and R$_4$ are each hydrogen;
R$_5$ is CH=CH$_2$;
R$_6$ and R$_7$ are each hydrogen;
X and X$_1$ are each CH;
m and n are each 1;
R$_8$ and R$_9$ are each NO$_2$, wherein R$_{10}$, R$_{11}$ and R$_{12}$ are each independently hydrogen or methyl; and
o is 0;
on a support effective for use in chromatographic separation.
* * * * *

UNITED STATES PATENT AND TRADEMARK OFFICE
CERTIFICATE OF CORRECTION

PATENT NO. : 5,256,293
DATED : October 26, 1993
INVENTOR(S) : William H. Pirkle, et al.

It is certified that error appears in the above-indentified patent and that said Letters Patent is hereby corrected as shown below:

Column 1, line 52: after "active" insert --.--

Column 3, line 36: after "place" insert --.--

Column 7, line 33: delete "="

Column 8, line 8: "R of" should read --R or--

Column 8, lines 9-10: "racenic" should read --racemic--

Column 9, line 42: after "contains" delete --to--

Column 13, line 48: "$N(R_{23})_3$" should read --$N(R_{23})_3^+$--

Column 15, line 3: "$N(R_{29})_3$" should read --$N(R_{29})_3^+$--

Column 15, line 3: "$CO_{r31}$" should read --$COR_{31}$--

Column 16, line 27: "from" should read --form--

Column 17, line 41: after "gel" insert --.--

Column 17, lines 49-59:  "    "

should read as:

-- 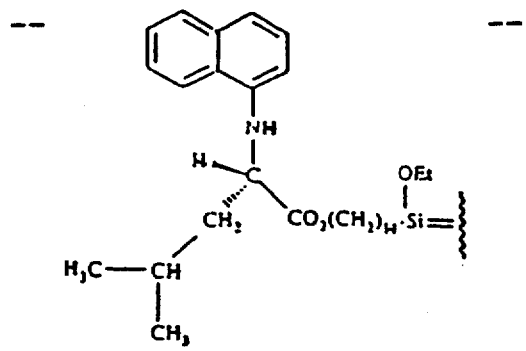 -- 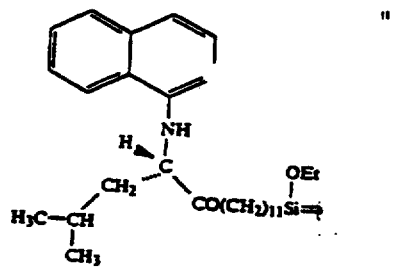

UNITED STATES PATENT AND TRADEMARK OFFICE
CERTIFICATE OF CORRECTION

PATENT NO. : 5,256,293
DATED : October 26, 1993
INVENTOR(S) : William H. Pirkle, et al.

It is certified that error appears in the above-indentified patent and that said Letters Patent is hereby corrected as shown below:

```
Column 18, line 34:   "HPL"  should read --HPLC--
Column 19, line 14:   "york" should read --York--
Column 19, line 20:   after "phase" insert --.--
Column 19, line 22:   after "membranes" insert --.--
Column 19, line 25:   after "selector" insert --.--
Column 19, line 31:   after "selector" insert --.--
Column 21, line 58:   after "minutes" insert --.--
Column 22, line 30:   after "entry" insert --.--
Column 23, line 2:    "(u)" should read --( d )--
Column 23, line 3:    after "analytes" insert --.--
Column 23, line 10:   after "obtained" insert --.--
Column 26, line 31:   "5µ 100" should read
--5µ/100--
Column 26, line 64:   after "phase" insert --.--
Column 26, line 64:   after "obtained" insert --.--
Column 27, line 2:    after "prepare" delete --to--
Column 28, line 43:   "Rexchorm" should read
--Rexchrom--
```

UNITED STATES PATENT AND TRADEMARK OFFICE
CERTIFICATE OF CORRECTION

PATENT NO. : 5,256,293
DATED : October 26, 1993
INVENTOR(S) : William H. Pirkle, et al It is certified that error appears in the above-indentified patent and that said Letters Patent is hereby corrected as shown below:

```
Column 29, line 22:   after "16" insert --.--
Column 30, line 20:   after "material" insert --.--
Column 30, line 21:   "6.58"  should read --(6.58--
Column 30, line 33:   "(S,3H)"  should read --(s,3H)--
```

UNITED STATES PATENT AND TRADEMARK OFFICE
CERTIFICATE OF CORRECTION

PATENT NO. : 5,256,293
DATED : October 26, 1993
INVENTOR(S) : William H. Pirkle, et al It is certified that error appears in the above-indentified patent and that said Letters Patent is hereby corrected as shown below:

Column 32, line 14: after "follows" insert --:--

Column 36, line 55: "sluted" should read --eluted--

Column 39, lines 29-35: " 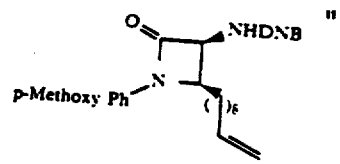 "

should read as

-- 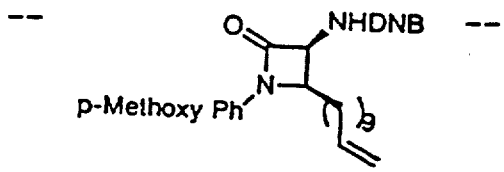 --

Signed and Sealed this

Twenty-seventh Day of September, 1994

Attest:

BRUCE LEHMAN

Attesting Officer     Commissioner of Patents and Trademarks